US009765320B2

(12) United States Patent
Koski et al.

(10) Patent No.: US 9,765,320 B2
(45) Date of Patent: *Sep. 19, 2017

(54) MODIFIED BETA-LACTAMASES AND METHODS AND USES RELATED THERETO

(71) Applicant: Synthetic Biologics, Inc., Rockville, MD (US)

(72) Inventors: Pertti Koski, Helsinki (FI); Ulla Airaksinen, Vantaa (FI); Katja Valimaki, Vantaa (FI)

(73) Assignee: SYNTHETIC BIOLOGICS, INC., Rockville, MD (US)

( * ) Notice: Subject to any disclaimer, the term of this patent is extended or adjusted under 35 U.S.C. 154(b) by 35 days.

This patent is subject to a terminal disclaimer.

(21) Appl. No.: 15/138,767

(22) Filed: Apr. 26, 2016

(65) Prior Publication Data

US 2016/0230160 A1 Aug. 11, 2016

Related U.S. Application Data

(63) Continuation of application No. 15/054,292, filed on Feb. 26, 2016, now Pat. No. 9,587,234, which is a continuation of application No. 14/676,559, filed on Apr. 1, 2015, now Pat. No. 9,301,996, which is a continuation of application No. 14/517,539, filed on Oct. 17, 2014, now Pat. No. 9,301,995, which is a continuation of application No. 14/047,882, filed on Oct. 7, 2013, now Pat. No. 8,894,994, which is a continuation of application No. 13/699,434, filed as application No. PCT/FI2011/050450 on May 17, 2011, now Pat. No. 9,034,602.

(30) Foreign Application Priority Data

May 24, 2010 (FI) .................................... 20105572

(51) Int. Cl.
| | | |
|---|---|---|
| C12N 9/86 | (2006.01) | |
| A61K 38/50 | (2006.01) | |
| A61K 31/43 | (2006.01) | |
| A61K 31/545 | (2006.01) | |
| A61K 45/06 | (2006.01) | |
| A61K 9/00 | (2006.01) | |
| A61K 9/48 | (2006.01) | |
| A61K 38/00 | (2006.01) | |

(52) U.S. Cl.
CPC .............. *C12N 9/86* (2013.01); *A61K 9/0053* (2013.01); *A61K 9/4891* (2013.01); *A61K 31/43* (2013.01); *A61K 31/545* (2013.01); *A61K 38/50* (2013.01); *A61K 45/06* (2013.01); *C12Y 305/02006* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2,890,986 | A | 6/1959 | Kraut et al. |
| 2,941,995 | A | 6/1960 | Doyle et al. |
| 2,982,696 | A | 5/1961 | Puetzer et al. |
| 3,070,511 | A | 12/1962 | Weitnauer |
| 3,150,059 | A | 9/1964 | Kleinschmidt et al. |
| 3,239,394 | A | 3/1966 | Walton |
| 3,488,729 | A | 1/1970 | Chauvette et al. |
| 3,499,909 | A | 3/1970 | Weissenburger et al. |
| 7,319,030 | B2 | 1/2008 | Koski et al. |
| 7,989,192 | B2 | 8/2011 | Kaariainen et al. |
| 2004/0248279 | A1 | 12/2004 | Sawada et al. |
| 2005/0158843 | A1 | 7/2005 | Koski et al. |
| 2005/0249716 | A1 | 11/2005 | Bourgeois et al. |
| 2009/0181004 | A1 | 7/2009 | Kaariainen et al. |
| 2009/0311234 | A1 | 12/2009 | Koski et al. |
| 2013/0216622 | A1 | 8/2013 | Koski et al. |

FOREIGN PATENT DOCUMENTS

| | | |
|---|---|---|
| EP | 0384559 A1 | 8/1990 |
| EP | 0420600 A2 | 4/1991 |
| EP | 0420600 A3 | 11/1992 |
| EP | 1564286 A1 | 8/2005 |
| FI | 59265 B | 3/1981 |

(Continued)

OTHER PUBLICATIONS

Altschul et al., "Gapped BLAST and PSI-BLAST: A New Generation of Protein Database Search Programs," Nucleic Acids Research, 1997, vol. 25, No. 17, pp. 3389-3402.

Ambler, "The structure of β-lactamases," Phil. Trans. R. Soc. Lond. B 289: 321-331 (1980).

Ambler et al., "A Standard Numbering Scheme for the Class A Beta-Lactamases," Biochem. J., 1991, 276, pp. 269-272.

Bonnet, "Growing Group of Extended-Spectrum β-Lactamases: the CTX-M Enzymes," Antimicrob. Agents Chemother. 48(1):1-14 (2004).

Bonomo et al., "β-Lactamase mutations far from the active site influence inhibitor binding," Biochim. Biophys. Acta 1247:121-125 (1995).

(Continued)

*Primary Examiner* — Robert Mondesi
*Assistant Examiner* — Todd M Epstein
(74) *Attorney, Agent, or Firm* — Morgan, Lewis & Bockius LLP

(57) ABSTRACT

The present invention relates to pharmaceuticals and modified beta-lactamases. Specifically, the invention relates to novel recombinant beta-lactamases and pharmaceutical compositions comprising the beta-lactamases.

Also, the present invention relates to methods for modifying a beta-lactamase, producing the beta-lactamase and treating or preventing beta-lactam antibiotic induced adverse effects. Furthermore, the present invention relates to the beta-lactamase for use as a medicament and to the use of the beta-lactamase in the manufacture of a medicament for treating or preventing beta-lactam antibiotics induced adverse effects.

Still further, the invention relates to a polynucleotide and a host cell comprising the polynucleotide.

14 Claims, 4 Drawing Sheets

(56) References Cited

FOREIGN PATENT DOCUMENTS

| | | |
|---|---|---|
| FI | 880017 A | 7/1988 |
| GB | 1241844 A | 8/1971 |
| GB | 1463513 A | 2/1977 |
| GB | 2199582 A | 7/1988 |
| WO | WO 88/07865 A1 | 10/1988 |
| WO | WO 93/13795 A1 | 7/1993 |
| WO | WO 97/03185 A1 | 1/1997 |
| WO | WO 03/040352 A1 | 5/2003 |
| WO | WO 2004/016248 A2 | 2/2004 |
| WO | WO 2005/078075 A2 | 8/2005 |
| WO | WO 2006/122835 A1 | 11/2006 |
| WO | WO 2007/147945 A1 | 12/2007 |
| WO | WO 2008/065247 A1 | 6/2008 |

OTHER PUBLICATIONS

Brogard et al., "Biliary Elimination of Ticarcillin Plus Clavulanic Acid (Ciaventin®)," Experimental and Clinical Study, International Journal of Clinical Pharmacology, Therapy and Toxicology, 1989, vol. 27, No. 3, pp. 135-144.

Broun et al., "Catalytic plasticity of fatty acid modification enzymes underlying chemical diversity of plant lipids," Science 1998, vol. 282: 1315-1317.

Bush, "Metallo-β-Lactamases: A Class Apart," Clinical Infectious Diseases, 1998; 27(Suppl 1):S48-53.

Bush et al., "A Functional Classification Scheme for β-Lactamases and Its Correlation with Molecular Structure," Antimicrobial Agents and Chemotherapy, Jun. 1995, vol. 39, No. 6, pp. 1211-1233.

Canica et al., "Phenotypic Study of Resistance of β-Lactamase-Inhibito-Resistant TEM Enzymes Which Differ by Naturally Occurring Variations and by Site-Directed Substitution at Asp276," Antimicrob. Agents Chemother. 42(6):1323-1328 (1998).

Carfi et al., "1.85 Å Resolution Structure of the Zinc II β-Lactamase from Bacillus cereus," Acta Cryst. (1998) D54: 313-323.

Carfi et al., "X-ray Structure of the Zn11 β-Lactamase from Bacteroides fragilis in an Orthorhombic Crystal Form," Acta. Cryst. (1998) D54: 47-57.

Carfi et al., "The 3-D structure of a zinc metallo-β-lactamase from Bacillus cereus reveals a new type of protein fold," The EMBO Journal, 1995, vol. 14 No. 20: 4914-4921.

Chambliss, "The forgotten dosage form: enteric coated tablets," (1983) Pharm Technol 7, 124-140.

Chen et al.,"β-Lactamase Genes of the Penicillin-Susceptible Bacillus anthracis Sterne Strain," J. Bacteriol. 185(3):823-830 (2003).

Chica et al., "Semi-rational approaches to engineering enzyme activity: combining the benefits of directed evolution and rational design," Curr. Opin. Biotechnol., 2005, vol. 16: 378-384.

Cole, "Hydrolysis of Penicillins and Related Compounds by the Cell-Bound Penicillin Acylase of Escherichia coli," (1969) Biochem. J. 115, 733-739.

Colombo et al., "The ybxl Gene of Bacillus Subtilis 168 Encodes a Class D β-Lactamase of Low Activity," Antimicrobial Agents and Chemotherapy, Feb. 2004, vol. 48, No. 2, pp. 484-490.

Concha et al., "Crystal Structure of the IMP-1 Metallo β-Lactamase from Pseudomonas aeruginosa and Its Complex with a Mercaptocarboxylate Inhibitor: Binding Determinants of a Potent, Broad-Spectrum Inhibitor," Biochemistry (2000) 39(15): 4288-4298.

Crawford, et al., "Over-expression, purification, and characterization of metallo-β-lactamase ImiS from Aeromonas veronii bv. sobria," Protein Expression and Purification 36 (2004) 272-279.

Davies and Abraham, "Separation, Purification and Properties of β-Lactamase I and β-Lactamase II from Bacillus cereus 569/H/9," (1974) Biochem. J. 143:115-127.

Delmas et al., "Structural Insights into Substrate Recognition and Product Expulsion in CTX-M Enzymes," J. Mol. Biol. 400:108-120 (2010).

Devos et al., "Practical limits of function prediction," Proteins: Structure, Function, and Genetics. 2000, vol. 41: 98-107.

Donskey, "Antibiotic Regimens and Intestinal Colonization with Antibiotic-Resistant Gram-Negative Bacilli," Clinical Infectious Diseases, 2006, 43 Suppl 2, pp. S62-S69.

Drawz et al., "The Role of a Second-Shell Residue in Modifying Substrate and Inhibitor Interactions in the SHV β-Lactamase: A Study of Ambler Position Asn276," Biochem. 48(21):4557-4566 (2009).

Finnish Patent Search Report from Finnish Patent Office for FI 20065431, dated Oct. 24, 2007.

Galleni et al., "Standard Numbering Scheme for Class B β-Lactamases," Antimicrobial Agents and Chemotherapy, Mar. 2001, vol. 45, No. 3, pp. 660-663.

Garau et al., "Update of the Standard Numbering Scheme for Class B β-Lactamases," Guest Commentary, Antimicrobial Agents and Chemotherapy, Jul. 2004, pp. 2347-2349, vol. 48, No. 7.

Garau et al., "A Metallo-β-lactamase Enzyme in Action: Crystal Structures of the Monozinc Carbapenemase CphA and its Complex with Biapenem," J. Mol. Biol. (2005) 345, 785-795.

Gazouli et al., "Effect of substitution of Asn for Arg-276 in the cefotaxime-hydrolyzing class A β-lactamase CTX-M-4," FEMS Microbiol. Lett. 168:289-293 (1998).

Gebhard et al., "Mapping the Distribution of Conformational Information Throughout a Protein Sequence," J. Mol. Biol., 2006, 358, pp. 280-288.

Giakkoupi et al., "Aspartic acid for asparagine substitution at position 276 reduces susceptibility to mechanism-based inhibitors in SHV-1 and SHV-5 β-lactamases," J. Antimicrobial. Chemother. 43:23-29 (1999).

Harmoinen et al., "Orally Administered Targeted Recombinant Beta-Lactamase Prevents Ampicillin-Induced Selective Pressure on the Gut Microbiota: A Novel Approach to Reducing Antimicrobial Resistance," Antimicrobial Agents and Chemotherapy, Jan. 2004, vol. 48, No. 1, pp. 75-79.

Harmoinen et al., "Enzymic Degradation of a β-Lactam Antibiotic, Ampicillin, in the Gut; A Novel Treatment Modality," Journal of Antimicrobial Chemotherapy, 2003,51, pp. 361-365.

Hata et al., "Substrate Deacylation Mechanisms of Serine-β-lactamases," Biol. Pharm. Bull. 29:2151-2159 (2006).

Herzberg, "Refined Crystal Structure of β-Lactamase from *Staphylococcus aureus* PC1 at 2.0 Å Resolution," J. Mol. Biol. 217:701-719 (1991).

Higgins et al., "In Vitro Activities of the β-Lactamase Inhibitors Clavulanic Acid, Sulbactam, and Tazobactam Alone or in Combination with β-Lactams against Epidemiologically Characterized Multidrug-Resistant Acinetobacter baumannii Strains," Antimicrobial Agents and Chemotherapy, May 2004, vol. 48, No. 5, pp. 1586-1592.

Hirschi A et al. "Campylobacter pylori, Gastritis and Ulcus pepticum," Wien. Klin. Wsch. 14:493-497 (1987).

Horton et al., "Engineering hybrid genes without the use of restriction enzymes: gene splicing by overlap extension," 1989, Gene 77:61-68 (1989).

Huber et al. "Chapter 2. Preparative Methods for 7-Aminocephalosporanic Acid and 6-Aminopenicillanic Acid," (1972) In: Flynn E, ed. Cephalosporins and Penicillins. New York: Academic Press, 27-73.

Hyman, "Anaphylactic Shock After Therapy With Penicillinase," (1959) JAMA 169, 593-594.

Illing et al., "Use of integrational plasmid excision to identify cellular localization of gene expression during sporulation in Bacillus subtilis," J. Bacteriol. 172(12):6937-6941 (1990).

International Search Report, PCT appl. No. PCT/FI93/00016 (dated May 7, 1993).

International Search Report, PCT appl. No. PCT/FI02/00861 (dated Feb. 11, 2003).

International Search Report, PCT appl. No. PCT/FI2007/050372 (dated Oct. 24, 2007).

International Search Report dated Mar. 3, 2008 for International Application No. PCT/FI2007/050627.

International Search Report, PCT appl. No. PCT/FI2011/050450 (dated Sep. 12, 2011).

(56) References Cited

OTHER PUBLICATIONS

Iserhard et al., "Epidemiology and Treatment of Gastric Campylobacter pylori Infection: more Questions than Answers," (1990) Hepato-Gastroenterol 37, 38-44.
Izui et al., "Large Exopenicillinase, Initial Extracellular Form Detected in Cultures of Bacillus licheniformis," Biochemistry, 1980, 19, pp. 1882-1886.
Kato et al., "Nucleotide Sequence of the β-Lactamase Gene of *Alkalophilic bacillus* sp. Strain 170," J. Gen. Microbiol. 131:3317-3324 (1985).
Katz, "Probiotics for the Prevention of Antibiotic-associated Diarrhea and Clostridium difficile Diarrhea," J. Clin. Gastroenterol., Mar. 2006, vol. 40, No. 3, pp. 249-255.
Kim and Buyn, "Purification and properties of ampicillin acylase from Pseudomonas melanogenum," (1990) Biochim Biophys Acta 1040, 12-18.
Kim et al., "Construction of spore mutants of Bacillus subtilis for the development as a host for foreign protein production," Biotechnology Letters 23:999-1004 (2001).
Kisselev L., "Polypeptide release factors in prokaryotes and eukaryotes: same function, different structure," Structure, 2002, vol. 10: 8-9.
Knox and Moews, "β-Lactamase of Bacillus licheniformis 749/C: Refinement at 2 Å Resolution and Analysis of Hydration," J. Mol. Bioi., 1991, 220, pp. 435-455.
Korhonen et al., "Milk Immunoglobulins and Complement Factors," British Journal of Nutrition, 2000, 84 Suppl 1, pp. S75-S80.
Kropp et al., "Metabolism of Thienamycin and Related Carbapenem Antibiotics by the Renal Dipeptidase, Dehydropeptidase-I," (1982) Antimicrob Agents Chemother 22, 62-70.
Kumakura et al., "Metabolic Fate of Clavulanic Acid and BRL 28500 in the Rat and Dog," Chemotherapy (Tokyo), 1986, 34 Suppl 4, pp. 187-201.
Lambert et al., "Susceptibility of Campylobacter pyloridis to 20 antimicrobial agents," (1986) Antimicrob Agents Chemother 30, (210): 510-511.
Li et al., "Bottlenecks in the expression and secretion of heterologous proteins in Bacillus subtilis," Res. Microbiol. 155:605-610 (2004).
Lim et al., "Cloning, Nucleotide Sequence, and Expression of the Bacillus cereus 5/B/6 β-Lactamase II Structural Gene," J. Bacteriol. 170:2873-2878 (1988).
Madan, "Methods of preparing microcapsules: interfacial polymerization," (1978) Pharm Technol 2, 68-75.
Madgwick and Waley, "β-Lactamase I from Bacillus cereus," Biochem. J. 248(3):657-662 (1987).
Madonna et al., "Nucleotide sequence of the β-lactamase I gene of Bacillus cereus strains 569/H and 5/B," Nucl. Acids Res. 15(4):1877 (1987).
Mandell and Sande, "Chapter 46. Antimicrobial Agents," (1990) In: Goodman.and Gilman's, The Pharmacological Basis of Therapeutics, 8th Edition. New York: Pergamon Press, 1065-1097.
Marciano et al., "Analysis of the plasticity of location of the Arg244 positive charge within the active site of the TEM-1 β-lactamase," Prot. Sci. 18:2080-2089 (2009).
Marmur, "A Procedure for the Isolation of Deoxyribonucleic Acid from Micro-organisms," J. Mol. Biol. (1961) 3: 208-218.
Matagne et al., "Ragged N-termini and other Variants of Class A β-Lactamases Analysed by Chromatofocusing," Biochem. J., 1991, 273, pp. 503-510.
Matagne et al., "Catalytic properties of class A β-lactamases: efficiency and diversity," Biochem. J. 330:581-598 (1998).
Mentula et al , "Inhibition of ampicillin-induced emergence of resistance in intestinal coliforms by targeted recombinant β-lactamase," International Journal of Antimicrobial Agents, (2004)24:555-561.
O'Callaghan et al., "Novel Method for Detection of β-Lactamases by Using a Chromogenic Cephalosporin Substrate," Antimicrobial Agents and Chemotherapy, Apr. 1972, vol. 1, No. 4, pp. 283-288.

Perez-Llarena et al., "Structure-function studies of arginine at position 276 in CTX-M β-lactamases," J. Antimicrob. Chemother. 61(4):792-797 (2008).
Pedraza-Reyes et al., "Temporal Regulation and Forespore-Specific Expression of the Spore Photoproduct Lyase Gene by Sigma-G RNA Polymerase during Bacillus subtilis Sporulation," J. Bacteriol. 176(13): 3983-3991. 1994.
Pluckthun and Knowles, "The consequence of of stepwise deletions from the signal-processing site of β-lactamase," J. Biol.Chem., 1987, vol. 262 (9): 3951-3957.
Rauws et al., "Campylobacter pyloridis-Associated Chronic Active Antral Gastritis," (1988) Gastroenterol 94, 33-40.
Rauws and Tytgat, "Cure of duodenal ulcer associated with eradication of Helicobacter pylori," (1990) Lancet 335, 1233-1235.
Rice et al., "β-Lactam Antibiotics and Gastrointestinal Colonization with Vancomycin-Resistant Enterococci," J. Infect. Dis., 2004, 189, pp. 1113-1118.
Sambrook and Russell. Molecular Cloning: A Laboratory Manual. "In vitro Amplification of DNA by the Polymerase Chain Reaction," vol. 2, Ch. 8, pp. 8.1-8.126. 2001.
Sande et al., "Chapter 44. Antimicrobial Agents," (1990) In: Goodman and Gilman's, The Pharmacological Basis of Therapeutics, 8th Edition. New York: Pergamon Press, 1018-1046.
Santillana et al., "Crystal structure of the carbapenemase OXA-24 reveals insights into the mechanism of carbapenem hydrolysis," Proc. Natl. Acad. Sci. USA, 104:5354-5359 (2007).
Santos et al., "Folding of an Abridged β-Lactamase," Biochemistry, 2004, 43, pp. 1715-1723.
Saunders et al., "Use of Chromosomal Integration in the Establishment and Expression of blaZ, a *Staphylococcus aureus* β-lactamase Gene, in Bacillus subtilis," J. Bacteriol. 157(3): 718-726. 1984.
Saves et al., "The Asparagine to Aspartic Acid Substitution at Position 276 of TEM-35 and TEM-36 Is Involved in the β-Lactamase Resistance to Clavulanic Acid," J. Biol. Chem. 270:18240-18245 (1995).
Sawa et al., "The Effect of Cefixime on Bacterial Flora in the Intestinal Tracts of Healthy Male Volunteers," (1985) Chemotherapy (Tokyo) 33, Suppl. 6, 169-180.
Search Report from National Board of Patents and Registration of Finland—Corresponding Finnish Application No. 20065757 (dated May 28, 2007).
Search Report from National Board of Patents and Registration of Finland—Corresponding Finnish Application No. 20105572 (dated 2010).
Sen et al., "Developments in directed evolution for improving enzyme functions," Appl. Biochem. Biotechnol., Aug. 18, 2007, vol. 143: 212-223.
Shimooka et al, "Absorption, Distribution, and Excretion of Sulbactam and Ampilcillin after Intravenous Administration in Rats and Dogs," Chemotherapy (Tokyo), 1988, 36 Suppl 8, pp. 66-80.
Simm et al., "Characterization of Monomeric L1 Metallo-β-lactamase and the Role of the N-terminal Extension in Negative Cooperativity and Antibiotic Hydrolysis," The Journal of Biological Chemistry (Jul. 2002) vol. 277 No. 27: 24744-24752.
Sjolund et al., "Long-Term Persistence of Resistant *Enterococcus* Species after Antibiotics to Eradicate Helicobacter pylori," Ann. Intern. Med. 139:483-487 (2003).
Stiefel et al., "Oral Administration of β-Lactamase Preserves Colonization Resistance of Piperacillin-Treated Mice," J. Infect. Dis., 2003, 188, pp. 1605-1609.
Stiefel et al., "Orally Administered Recombinant Metallo-β-Lactamase Preserves Colonization Resistance of Piperacillin-Tazobactam-Treated Mice," Antimicrobial Agents and Chemotherapy, Dec. 2005, vol. 49, No. 12, pp. 5190-5191.
Sullivan et al., "Effect of Antimicrobial Agents on the Ecological Balance of Human Microflora," Lancet Infect. Dis., 2001, vol. 1, pp. 101-114.
Supplementary EP Search Report relating to Corresponding EP 07765926.6, dated Mar. 4, 2010.
Tarkkanen et al., "P1A Recombinant β-Lactamase Prevents Emergence of Antimicrobial Resistance in Gut Microflora of Healthy Subjects during Intravenous Administration of Ampicillin," Antimicrob. Agents Chemother. 53:2455-2462 (2009).

(56) References Cited

OTHER PUBLICATIONS

Therapeutic Drugs (1991), Dollery C, ed. Edinburgh: Churchill Livingstone, "Ceftriaxone (sodium)," c 127-c133.
Tranier et al., "The High Resolution Crystal Structure for Class A β-Lactamase PER-1 Reveals the Bases for Its Increase in Breadth of Activity," J. Biol. Chem. 275:28075-28082 (2000).
Walsh et al., "Metallo-β-Lactamases: the Quiet before the Storm?" Clinical Microbiology Reviews (Apr. 2005) vol. 18 No. 2: 306-325.
Walther-Rasmussen et al., "Terminal truncations in Amp C β-lactamase from a clinical isolate of Pseudomonas aeruginosa," Eur. J. Biochem.(1999) 263: 478-485.
Westphal et al., "Assessment of Biliary Excretion of Piperacilin-Tazobactam in Humans," Antimicrobial Agents and Chemotherapy, Aug. 1997, vol. 41, No. 8, pp. 1636-1640.
Whisstock et al., "Prediction of protein function from protein sequence," Q. Rev. Biophysics., 2003, vol. 36 (3): 307-340.
Wildfeuer et al., "Pharmacokinetics of Sulbactam and Ampicillin Intravenously Applied in Combination to Healthy Volunteers and Patients", Arzneimittei-Forschung, 1988, vol. 38, No. 11, pp. 1640-1643.
Wishart et al., "A single mutation converts a novel phosphotyrosine binding domain into a dual-specificity phosphatase," J. Biol. Chem., 1995, vol. 270(45): 26782-26785.
Witkowski et al., "Conversion of β-ketoacyl synthase to a Malonyl Decarboxylase by replacement of the active cysteine with glutamine," Biochemistry, 1999, vol. 38: 11643-11650.
Knox, "Extended-spectrum and inhibitor-resistant TEM-Type β-lactamases: Mutations, Specificity, and Three-Dimensional Structure," Antimicrob. Agents Chemother., 1995, 39, 2593-2601.

```
atgattcaaaaacgaaagcggacagtttcgttcagacttgtgcttatgtgcacgctgtta
 M   I   Q   K   R   K   R   T   V   S   F   R   L   V   L   M   C   T   L   L
                                                   HindIII site
tttgtcagtttgccgattacaaaaacatcagcgcaagcttccaagacggagatgaaagat
 F   V   S   L   P   I   T   K   T   S   A   Q   A   S   K   T   E   M   K   D
                                              -1  +1              +6
gattttgcaaaacttgaggaacaatttgatgcaaaactcgggatctttgcattggataca
 D   F   A   K   L   E   E   Q   F   D   A   K   L   G   I   F   A   L   D   T
ggtacaaaccggacggtagcgtatcggccggatgagcgttttgcttttgcttcgacgatt
 G   T   N   R   T   V   A   Y   R   P   D   E   R   F   A   F   A   S   T   I
aaggctttaactgtaggcgtgcttttgcaacagaaatcaatagaagatctgaaccagaga
 K   A   L   T   V   G   V   L   L   Q   Q   K   S   I   E   D   L   N   Q   R
ataacatatacacgtgatgatcttgtaaactacaacccgattacggaaaagcacgttgat
 I   T   Y   T   R   D   D   L   V   N   Y   N   P   I   T   E   K   H   V   D
acgggaatgacgctcaaagagcttgcggatgcttcgcttcgatatagtgacaatgcggca
 T   G   M   T   L   K   E   L   A   D   A   S   L   R   Y   S   D   N   A   A
cagaatctcattcttaaacaaattggcggacctgaaagtttgaaaaaggaactgaggaag
 Q   N   L   I   L   K   Q   I   G   G   P   E   S   L   K   K   E   L   R   K
attggtgatgaggttacaaatcccgaacgattcgaaccagagttaaatgaagtgaatccg
 I   G   D   E   V   T   N   P   E   R   F   E   P   E   L   N   E   V   N   P
ggtgaaactcaggataccagtacagcaagagcacttgtcacaagccttcgagcctttgct
 G   E   T   Q   D   T   S   T   A   R   A   L   V   T   S   L   R   A   F   A
cttgaagataaacttccaagtgaaaaacgcgagcttttaatcgattggatgaaacgaaat
 L   E   D   K   L   P   S   E   K   R   E   L   L   I   D   W   M   K   R   N
accactggagacgccttaatccgtgccggtgtgccggacggttgggaagtggctgataaa
 T   T   G   D   A   L   I   R   A   G   V   P   D   G   W   E   V   A   D   K
actggagcggcatcatatggaacccggaatgacattgccatcatttggccgccaaaagga
 T   G   A   A   S   Y   G   T   R   N   D   I   A   I   I   W   P   P   K   G
gatcctgtcgttcttgcagtattatccagcagggataaaaaggacgccaagtatgataat
 D   P   V   V   L   A   V   L   S   S   R   D   K   K   D   A   K   Y   D   N
aaacttattgcagaggcaacaaaggtggtaatgaaagccttaaacatgaacggcaaataa
 K   L   I   A   E   A   T   K   V   V   M   K   A   L   N   M   N   G   K   *
```

Figure 2.

```
atgattcaaaaacgaaagcggacagtttcgttcagacttgtgcttatgtgcacgctgtta
 M  I  Q  K  R  K  R  T  V  S  F  R  L  V  L  M  C  T  L  L
tttgtcagtttgccgattacaaaaacatcagcgcaagcttccaagacggagatgaaagat
 F  V  S  L  P  I  T  K  T  S  A  Q  A  S  K  T  E  M  K  D
                                    -1 +1
gattttgcaaaacttgaggaacaatttgatgcaaaactcgggatctttgcattggataca
 D  F  A  K  L  E  E  Q  F  D  A  K  L  G  I  F  A  L  D  T
ggtacaaaccggacggtagcgtatcggccggatgagcgttttgcttttgcttcgacgatt
 G  T  N  R  T  V  A  Y  R  P  D  E  R  F  A  F  A  S  T  I
aaggctttaactgtaggcgtgcttttgcaacagaaatcaatagaagatctgaaccagaga
 K  A  L  T  V  G  V  L  L  Q  Q  K  S  I  E  D  L  N  Q  R
ataacatatacacgtgatgatcttgtaaactacaacccgattacggaaaagcacgttgat
 I  T  Y  T  R  D  D  L  V  N  Y  N  P  I  T  E  K  H  V  D
acgggaatgacgctcaaagagcttgcggatgcttcgcttcgatatagtgacaatgcggca
 T  G  M  T  L  K  E  L  A  D  A  S  L  R  Y  S  D  N  A  A
cagaatctcattcttaaacaaattggcggacctgaaagtttgaaaaaggaactgaggaag
 Q  N  L  I  L  K  Q  I  G  G  P  E  S  L  K  K  E  L  R  K
attggtgatgaggttacaaatcccgaacgattcgaaccagagttaaatgaagtgaatccg
 I  G  D  E  V  T  N  P  E  R  F  E  P  E  L  N  E  V  N  P
ggtgaaactcaggataccagtacagcaagagcacttgtcacaagccttcgagcctttgct
 G  E  T  Q  D  T  S  T  A  R  A  L  V  T  S  L  R  A  F  A
cttgaagataaacttccaagtgaaaaacgcgagcttttaatcgattggatgaaacgacgc
 L  E  D  K  L  P  S  E  K  R  E  L  L  I  D  W  M  K  R  R
accactggagacgccttaatccgtgccggtgtgccggacggtttgggaagtggctgataaa
 T  T  G  D  A  L  I  R  A  G  V  P  D  G  W  E  V  A  D  K
actggagcggcatcatatggaacccggaatgacattgccatcatttggccgccaaaagga
 T  G  A  A  S  Y  G  T  R  N  D  I  A  I  I  W  P  P  K  G
gatcctgtcgttcttgcagtattatccagcagggataaaaaggacgccaagtatgatcgc
 D  P  V  V  L  A  V  L  S  S  R  D  K  K  D  A  K  Y  D  R
aaacttattgcagaggcaacaaaggtggtaatgaaagccttaaacatgaacggcaaataa
 K  L  I  A  E  A  T  K  V  V  M  K  A  L  N  M  N  G  K  *
```

Figure 3.

MODIFIED BETA-LACTAMASES AND METHODS AND USES RELATED THERETO

CROSS REFERENCE TO RELATED APPLICATIONS

This application is a continuation of U.S. patent application Ser. No. 15/054,292, filed Feb. 26, 2016, which is a continuation of U.S. patent application Ser. No. 14/676,559, filed Apr. 1, 2015 (now U.S. Pat. No. 9,301,996), which is a continuation of U.S. patent application Ser. No. 14/517,539, filed Oct. 17, 2014 (now U.S. Pat. No. 9,301,995), which is a continuation of U.S. patent application Ser. No. 14/047,882, filed Oct. 7, 2013 (now U.S. Pat. No. 8,894,994), which is a continuation of U.S. patent application Ser. No. 13/699,434, filed Nov. 21, 2012 (now U.S. Pat. No. 9,034,602), which is a U.S. National Stage Application of International Application No. PCT/FI2011/050450, filed May 17, 2011, which claims priority from Finnish Patent Application No. 20105572, filed May 24, 2010, the entire contents of all of which are incorporated herein by reference.

FIELD OF THE INVENTION

The present invention relates to pharmaceuticals and modified beta-lactamases. Specifically, the invention relates to novel recombinant lactamases and pharmaceutical compositions comprising the beta-lactamases.

Also, the present invention relates to methods for modifying a beta-lactamase, producing the beta-lactamase and treating or preventing beta-lactam antibiotic induced adverse effects. Furthermore, the present invention relates to the beta-lactamase for use as a medicament and to the use of the beta-lactamase in the manufacture of a medicament for treating or preventing beta-lactam antibiotics induced adverse effects.

Still further, the invention relates to a polynucleotide and a host cell comprising the polynucleotide.

BACKGROUND OF THE INVENTION

Beta-lactam antibiotics are characterized by a beta-lactam ring in their molecular structure. The integrity of the beta-lactam ring is essential for the biological activity, which results in the inactivation of a set of transpeptidases that catalyze the final cross-linking reactions of peptidoglycan synthesis. Members of the beta-lactam antibiotics family comprise penicillins, cephalosporins, clavams (or oxapenams), cephamycins and carbapenems.

Beta-lactamases are bacterial defensive enzymes that hydrolyze beta-lactam antibiotics. The production of beta-lactamases is a predominant mechanism to confer beta-lactam resistance in Gram-negative bacteria. Beta-lactamases catalyse very efficiently irreversible hydrolysis of the amide bond of the beta-lactam ring resulting in biologically inactive product(s).

Because of the diversity of enzymatic characteristics of different beta-lactamase types, several classification systems have been proposed for their categorising. The classifications are based on two major approaches, which are functional and molecular classifications.

The functional classification scheme of beta-lactamases proposed by Bush et al., (1995, Antimicrob. Agents Chemother. 39: 1211-1233) defines four beta-lactamase groups, which are based on their substrate and inhibitor profiles. Group 1 consists of cephalosporinases that are not well inhibited by clavulanic acid. Group 2 consists of penicillinases, cephalosporinases and broad-spectrum beta-lactamases that are generally inhibited by active site-directed beta-lactamase inhibitors. Group 3 consists of metallo-beta-lactamases that hydrolyze penicillins, cephalosporins and carbapenems, and that are poorly inhibited by almost all beta-lactam-containing molecules. Group 4 consists of penicillinases that are not well inhibited by clavulanic acid. Subgroups have also been defined according to rates of hydrolysis of carbenicillin or cloxacillin (oxacillin) by group 2 penicillinases.

The most widely used classification is Ambler classification which divides beta-lactamases into four classes (A, B, C, D) and is based on their amino-acid sequences (Ambler 1980, Philos Trans R Soc Lond B Biol Sci. 289: 321-331). Classes A, C, and D gather evolutionarily distinct groups of serine beta-lactamase enzymes, and class B the zinc-dependent ("EDTA-inhibited") beta-lactamase enzymes (Ambler R. P. et al., 1991, Biochem J. 276: 269-270). Classes A, C, and D belong to serine beta-lactamases, in which the hydrolysis of the beta-lactam is mediated by serine in an active site. Serine beta-lactamases are related to DD peptidases (D-alanyl-D-alanine carboxypeptidase), the target enzyme of beta-lactams. The mechanism by which serine beta-lactamases hydrolyze beta-lactam antibiotics is believed to follow a three-step pathway including a non-covalent Henri-Michaelis complex, a covalent acyl-enzyme intermediate and deacylation (Matagne et al., 1998, Biochem J 330:581-598). Acylation mechanism is considered to be a common mechanism for all serine beta-lactamase groups whereas, on the basis of theoretical calculations, the substrate deacylation mechanisms of serine beta-lactamase of classes A, C and D appear to differ from each other. Deacylation mechanisms have both common and group specific elementary processes (Hata M et al., 2006, Biol Pharm Bull. 29: 2151-2159).

*Bacillus* spp. serine beta-lactamases and TEM-1, SHV-1 and CTX-M families have primarily been classified as class A beta-lactamases and as penicillinases that possess good capability to hydrolyze e.g. penicillin and ampicillin. The class A beta-lactamases were first identified in penicillin resistant St. *aureus* in the 1940s. A plasmid-borne penicillin resistance gene, TEM-1, was discovered in *E. coli* 20 years later. Later on, serine beta-lactamases were also shown to evolve the ability to hydrolyze most cephalosporins and further specialize at hydrolysing a specific subset of cephalosporins. Most of these extended-spectrum beta-lactamases (ESBL) are derivates of TEM-1, TEM-2 or SHV-1 enzymes. Recently there are increasing numbers of reports that describe the vast emergence of CTX-M enzymes, a new group of class A ESBLs. Nowadays, CTX-M enzymes are the most frequently observed ESBLs and are sub-classified into five major families. CTX-M enzymes have a wide substrate range including penicillin and the first, second and third generation cephalosporins (Bonnet, R. 2004. Antimicrob Agents Chemother. 48:1-14).

While the sequence similarity between the class A beta-lactamases (TEM, SHV, CTX-M, *Bacillus* spp. beta-lactamases) is moderate, the crystal structures of all serine beta-lactamases show a particularly high similarity (Matagne et al., 1998, Biochem J 330:581-598; Tranier S. et al., 2000, J Biol Chem, 275: 28075-28082; Santillana E. et al., 2007, Proc Natl Acad Sci. USA. 104: 5354-5359). The enzymes are composed of two domains. One domain consists of a five-stranded beta sheet packed against three alpha helices whilst the second domain, an alpha domain, is composed of eight alpha helices. The active site pocket is part of the interface between these two domains and is limited by the omega loop. The omega loop is a conserved structural element of all class A beta-lactamases and is essentially involved in catalytic reaction (FIG. 1).

Several conserved peptide sequences (elements) related to catalysis or recognition of the substrate have been identified in class A beta-lactamases. The first conserved element 70-Ser-X-X-Lys-73 (SEQ ID NO: 17) (Ambler classification) includes the active serine residue at location 70 in alpha helix$_2$ and lysine at position 73. The second conserved element is a SXN loop in an alpha domain (at positions between 130 and 132 according to Ambler classification), where it forms one side of a catalytic cavity. The third conserved element (at positions between 234 and 236 according to Ambler classification) is on the innermost strand of the beta-sheet$_3$ and forms the other side of the catalytic cavity. The third conserved element is usually KTG. However, in some exceptional cases, lysine (K) can be replaced by histidine (H) or arginine (R), and in several beta-lactamases, threonine (T) can be substituted by serine (S) (Matagne et al., 1998. Biochem J 330:581-598).

Beta-lactamase mediated resistance to beta-lactams is widely spread among pathogen and commensal microbiota, because of abundant use of beta-lactams in recent decades. Indeed, antibiotic resistance is a well-known clinical problem in human and veterinary medicine, and hundreds of different beta-lactamases derived from Gram-positive and Gram-negative bacteria have been purified and characterized in the scientific literature. Because the use of antimicrobials has not reduced and furthermore, antimicrobial resistance has become part of the everyday life, new approaches are invariably and urgently required for solving these medical problems.

The intestinal microbiota of humans is a complex bacterial community that plays an important role in human health, for example, by stimulating the immune response system, aiding in digestion of food and preventing the overgrowth of potential pathogen bacteria. Antimicrobial agents e.g. beta-lactams are known to have effect on normal microbiota. The efficacy of antimicrobial agents to promote changes of normal intestinal microbiota is associated with several factors including drug dosage, route of administration and pharmacokinetics/dynamics and properties of antibiotics (Sullivan Å. et al., 2001, Lancet 1:101-114). Even though the intestinal microbiota have a tendency to revert to normal after completion of antibiotic treatment, long term persistence of selected resistant commensal bacteria has been reported (Sjölund M. et al., 2003, Ann Intern Med. 139:483-487). Such persistence and the exchange of antibiotic resistance genes make the commensal microbiota a putative reservoir of antibiotic resistance genes.

Certain parentally administered beta-lactams like ampicillin, ceftriaxone, cefoperazone, and piperacillin are in part eliminated via biliary excretion into the proximal part of the small intestine (duodenum). Residual unabsorbed beta-lactams in the intestinal tract may cause an undesirable effect on the ecological balance of normal intestinal microbiota resulting in antibiotic-associated diarrhea, overgrowth of pathogenic bacteria such as vancomycin resistant enterococci (VRE), extended-beta-lactamase producing Gram-negative bacilli (ESBL), *Clostridium difficile*, and fungi, and selection of antibiotic-resistance strains among both normal intestinal microbiota and potential pathogen bacteria.

The therapeutic purpose of beta-lactamases is inactivating unabsorbed antibiotics in the gastrointestinal tract (GIT), thereby maintaining a normal intestinal microbiota and preventing its overgrowth with potentially pathogenic micro-organisms (WO 93/13795).

There are at least three requirements for beta-lactamase drug products, which are suitable for GIT targeted therapy. The first requirement is to preserve enzymatic activity under conditions prevailing in the GIT. Resistance against proteolytic breakdown by various proteases secreted from various glands into the GIT is a quintessential precondition for the feasibility of beta-lactamase therapy. Another important consideration is the range of pH values prevailing in the different compartments of the small intestine. These pH values usually vary between 5 (duodenum) and 7.5 (ileum). Hence, in order to qualify as candidates for the intended therapeutic purpose, a beta-lactamase needs to exhibit high enzymatic activity over the pH range 5-7.5.

The second requirement of a beta-lactamase or a product thereof is to hydrolyze beta-lactam efficiently. The concentration of a beta-lactam antibiotic in small intestinal chyme during an antibiotic treatment episode is mostly related to the elimination of the particular beta-lactam via biliary excretion. A suitable beta-lactamase needs to have kinetic parameters that enable it to effectively hydrolyze lower GIT beta-lactam concentrations below levels causing alterations in intestinal microbiota. The ideal set of kinetic parameters consists of a numerical low value for the Michaelis constant $K_M$, combined with a numerically high value for the maximum reaction rate $V_{max}$. A high $V_{max}$ value is required in order to provide a sufficient degree of breakdown capacity, while a low $K_M$ value is needed to ensure beta-lactam degrading activity at low substrate concentrations.

The third requirement of a beta-lactamase or a product thereof is to tolerate the conditions, such as relatively high temperatures, in the manufacturing of pharmaceutical compositions. Moreover, in the production process, the mixing dispersion of aqueous excipients and drug substance requires a high degree of solubility at suitable pH.

An enzymatic therapy, named Ipsat P1A, is being developed for the prevention of the adverse effects of β-lactam antibiotics inside the gut. Ipsat P1A delivery system has been designed to inactivate parenterally given penicillin group beta-lactams (e.g. penicillin, amoxicillin ampicillin and piperacillin) with or without beta-lactamase inhibitors (e.g. tazobactam, sulbactam, clavulanic acid) excreted via biliary system (WO 2008065247; Tarkkanen, A. M. et al., 2009, Antimicrob Agents Chemother. 53:2455-2462). The P1A enzyme is a recombinant form of *Bacillus licheniformis* 749/C small exo beta-lactamase (WO 2008065247) which belongs to class A and is grouped to subgroup 2a in functional classification. *B. licheniformis* beta-lactamase and its P1A derivate are considered as penicillinases which have high hydrolytic capacity to degrade e.g. penicillin, ampicillin, amoxicillin or piperacillin (Table 1) and they are generally inhibited by active site-directed beta-lactamase inhibitors such as clavulanic acid, sulbactam or tazobactam (Bush K. et al., 1995, Antimicrob Agents Chemother 39: 1211-1233).

However, the P1A enzyme has only a very limited capacity to inactivate beta-lactam antibiotics that belong to the cephalosporin or the carbapenem group. Because the employed beta-lactamases possess poor activity to cephalosporins, they can not be applied in conjunction with parenteral cephalosporin therapy for inactivation of unabsorbed beta-lactam in the small intestinal tract.

Therefore, new beta-lactamases or derivates of P1A with extended substrate profile, for example as seen in metallo-beta-lactamases, are indispensable.

The present invention provides novel genetically tailored derivates of P1A beta-lactamase and furthermore, novel methods for modifying and producing beta-lactamases.

BRIEF DESCRIPTION OF THE INVENTION

The new recombinant derivates of P1A beta-lactamase of the invention fulfill the above-mentioned three requirements of suitable beta-lactamases (i.e. have abilities to preserve enzymatic activity, hydrolyze beta-lactams efficiently and tolerate conditions in the manufacturing of the pharmaceutical compositions) and furthermore, have extended substrate profiles. The beta-lactamases of the invention may also be used in conjunction with parenteral cephalosporin therapy for inactivating biliary eliminated beta-lactam in the small intestinal tract.

The present invention highlights the preliminary and preclinical studies of a new Ipsat P3A pharmaceutical protein (a D276N substituted derivate of P1A) and presents a single drug substance dose.

The present invention enables rapid and efficient methods for modifying beta-lactamases and for producing them. Furthermore, by the present invention more effective and specific treatments become available.

The enzymes of the invention are suitable for large scale manufacturing for a drug substance for treating or preventing adverse effects induced by various groups of beta-lactam antibiotics.

The object of the present invention is to provide novel beta-lactamases, especially beta-lactamases of *B. licheniformis*, and to provide products, methods and uses related to the beta-lactamases. Tools for further developments in pharmaceutical industries are also presented by the invention.

The present invention relates to a beta-lactamase comprising an amino acid sequence having at least 60% sequence identity with SEQ ID NO: 1 and having a hydrophilic amino acid residue at a position of SEQ ID NO: 1 corresponding to position 276 according to Ambler classification, or a variant or fragment thereof.

The invention also relates to a pharmaceutical composition comprising the beta-lactamase of the invention.

The invention also relates to a method of modifying a beta-lactamase comprising an amino acid sequence having at least 60% sequence identity with SEQ ID NO: 1, wherein an amino acid of the beta-lactamase at a position of SEQ ID NO: 1 corresponding to position 276 according to Ambler classification is replaced with a hydrophilic amino acid.

Furthermore, the invention relates to a method of producing the beta-lactamase, wherein the method comprises the following steps:
 i) providing a gene encoding the beta-lactamase of the invention;
 ii) transforming a host cell with the gene;
 iii) obtaining a host cell that produces the beta-lactamase;
 iv) recovering the beta-lactamase.

Furthermore, the invention relates to a method of treating or preventing beta-lactam antibiotic induced adverse effects in the gastro-intestinal tract by administering beta-lactamase of the invention simultaneously or sequentially with a beta-lactam antibiotic to a subject.

Still further, the present invention relates to the beta-lactamase for use as a medicament.

Still further, the present invention relates to a use of the beta-lactamase in the manufacture of a medicament for treating or preventing beta-lactam antibiotics induced adverse effects in the gastro-intestinal tract.

Still further, the invention relates to a polynucleotide, which comprises a sequence of any one of SEQ ID NO:s 2 or 4 or a degenerate thereof, or it encodes the beta-lactamase of the invention. The invention also relates to a host cell comprising the polynucleotide.

BRIEF DESCRIPTION OF THE FIGURES

FIG. 2 shows the nucleotide and deduced amino acid sequences of D276N beta-lactamase gene of *Bacillus licheniformis* (P1A derivate). The amino acid sequence corresponds to sequence SEQ ID NO: 3, wherein Xaa is asparagine (Asn). The nucleotide sequence corresponds to sequence SEQ ID NO: 4, wherein the nucleotide triplet nnn is aat. The open reading frame encodes a 299 amino acid polypeptide possessing a 31 amino acid long signal sequence (underlined) of the amyQ gene derived from the pKTH141 secretion vector (WO 2008/065247). The predicted signal peptidase cleavage site is after alanine (A) at position −1. The HindIII cloning site that encodes an $NH_2$-QAS extension is expressed as bold. The mature D276N mutant enzyme starts from glutamine (Q) at a position of +1. Thus, the mature D276N mutant beta-lactamase comprises 268 amino acid residues including the $NH_2$-QAS extension encoded by HindIII. A single amino acid substitution of aspartic acid (D) to asparagine (N) is located at the position 280 (expressed as a bold character) corresponding to the position of 276 in the Ambler classification system and corresponding to amino acid position 249 in sequence SEQ ID NO: 3.

The $NH_2$-terminal sequence of purified D276N mutant enzyme was determined by automated Edman degradation in a protein sequencer. Analysis demonstrated that the D276N mutant enzyme lacks NH2-QASKT-pentapeptide (SEQ ID NO: 18) at its deduced amino terminus in a manner similar to that of its parent NA enzyme (WO 2008/065247). The major fraction of the purified D276N mutant enzyme, which has been utilized in examples 4 and 6 of this application, initiates from glutamic acid at position +6 and is composed of 263 amino acid residues with a molecular mass of 29 272.

FIG. 3 shows the nucleotide and deduced amino acid sequences of D276R substituted beta-lactamase gene of P1A derived from *Bacillus licheniformis*. The amino acid sequence corresponds to sequence SEQ ID NO: 3, wherein Xaa is arginine (Arg). The nucleotide sequence corresponds to sequence SEQ ID NO: 4, wherein the nucleotide triplet nnn is cgc.

Figure 4:
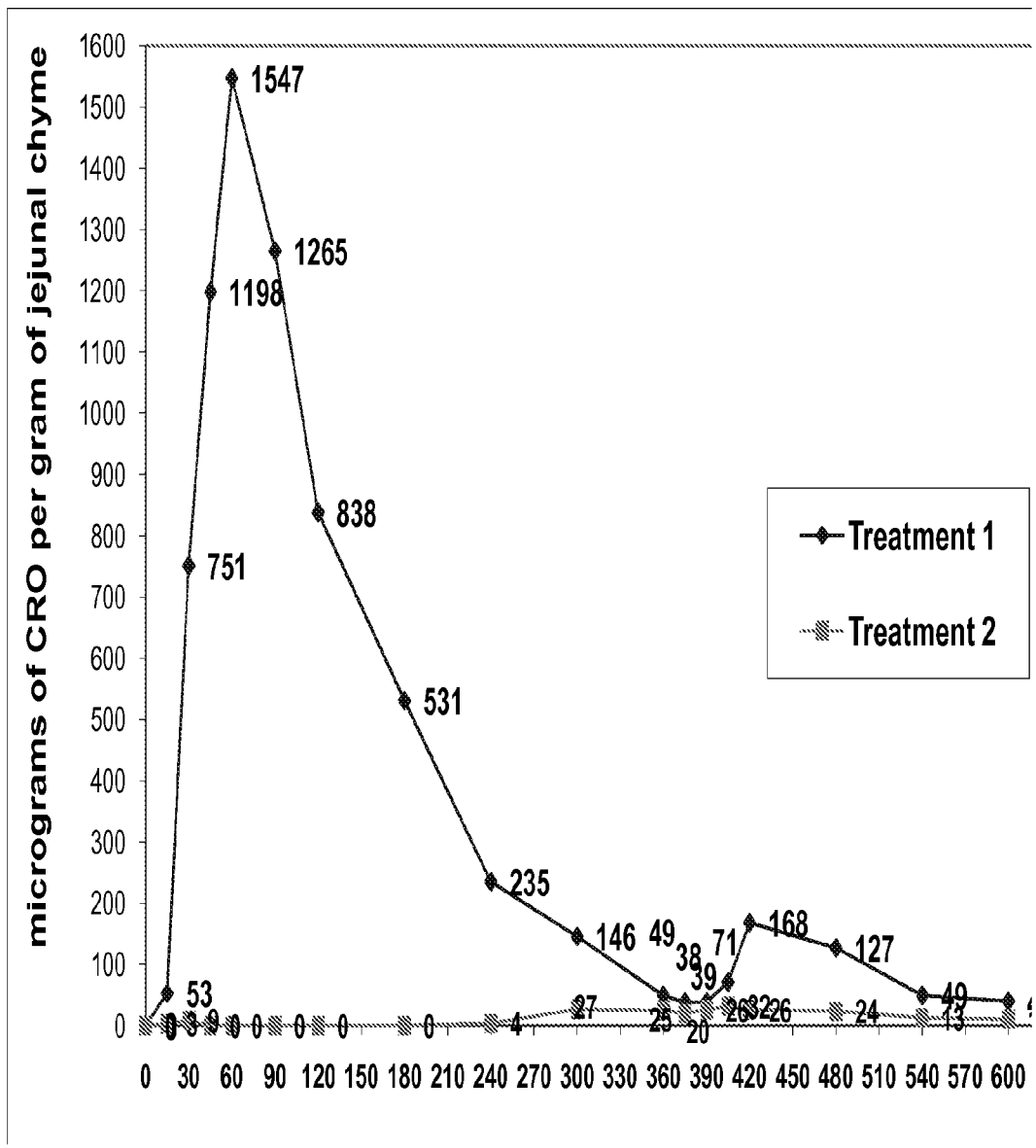

FIG. 4 shows the effect of orally administered enteric coated D276N substituted beta-lactamase (P3A) pellets on the concentrations of ceftriaxone in jejunal chyme of beagle dogs (n=5) after intravenous administration of ceftriaxone (30 mg of ceftriaxone per kg of body weight) (closed squares). Beta-lactamase pellets were received 10 minutes prior to ceftriaxone injection. Closed diamonds represent jejunal ceftriaxone concentrations achieved after a single dose of ceftriaxone (i.v.) without beta-lactamase treatment.

DETAILED DESCRIPTION OF THE INVENTION

Beta-lactamases have been used in inactivating unabsorbed beta-lactams in the gastrointestinal tract in order to prevent the beta-lactam induced adverse effects including alterations in intestinal normal microbiota and the overgrowth of beta-lactam resistant bacteria (WO 9313795, WO 2008065247, WO 2007147945. The present invention now provides a modified beta-lactamase of *Bacillus licheniformis*, which shows a surprising altered substrate profile.

As used herein, a beta-lactamase refers to an enzyme, which hydrolyzes beta-lactams. Hydrolysis of the amide bond of the beta-lactam ring makes the antimicrobial agents biologically inactive. As used herein, class A beta-lactamases (Ambler classification) refer to serine beta-lactamases, in which hydrolysis of beta-lactam is mediated by serine in the active site, usually at amino acid position 70 in the alpha helix$_2$. Class A beta-lactamases include but are not limited to Len-1, SHV-1, TEM-1, PSE-3/PSE-3, ROB-1, *Bacillus cereus* such as 5/B type 1, 569/H type 1 and 569/H type 3, *Bacillus anthrasis* sp, *Bacillus licheniformis* such as PenP, *Bacillus weihenstephanensis, Bacillus clausii, Staphylococcus aureus*, PC1, Sme-1, NmcA, IMI-, PER-, VEB-, GES-, KPC-, CME- and CTX-M types beta-lactamases.

Sequence Identity of Peptides and Polynucleotides

The amino acid sequences of the mutant beta-lactamase of the present invention (D276X, P1A derivate) are set forth as SEQ ID NO: 1 and SEQ ID NO: 3. The corresponding nucleotide sequences are set forth as SEQ ID NO: 2 and SEQ ID NO: 4. SEQ ID NO: 1 sets forth the amino acid sequence taking part in the formation of secondary structure of the beta-lactamase. SEQ ID NO: 3 sets forth the full length amino acid sequence of the protein, including the 31 amino acids long signal sequence.

A beta-lactamase of the invention may comprise an amino acid sequence having at least 30, 35, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9 or 100% identity with SEQ ID NO: 1 or 3.

According to a specific embodiment of the invention, the peptide has at least 30, 35, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9 or 100% identity with SEQ ID NO: 1 or 3.

In one preferred embodiment of the invention, the beta-lactamase of the invention comprises an amino acid sequence having at least 60% sequence identity with SEQ ID NO: 1. In another preferred embodiment of the invention the beta-lactamase has at least 60% sequence identity with SEQ ID NO: 1 or 3.

In one embodiment of the invention the beta-lactamase comprising an amino acid sequence having any above-mentioned sequence identity with SEQ ID NO: 1, has a hydrophilic amino acid selected from a group consisting of arginine (R), histidine (H), lysine (K), asparagine (N), glutamine (Q), serine (S) and threonine (T) at a position of SEQ ID NO: 1 corresponding to position 276 according to Ambler classification.

In a preferred embodiment of the invention the peptide has the sequence shown in SEQ ID NO: 1 or 3. In one embodiment of the invention, the beta-lactamase has the sequence as shown in SEQ ID NO: 1 or 3, wherein a hydrophilic amino acid residue at a position corresponding to position 276 according to Ambler classification (marked as Xaa in SEQ ID NO: 1 or 3) is an arginine (R, Arg). In another embodiment of the invention, the beta-lactamase has the sequence as shown in SEQ ID NO: 1 or 3, wherein a hydrophilic amino acid residue at a position corresponding to position 276 according to Ambler classification (marked as Xaa in SEQ ID NO: 1 or 3) is an asparagine (N, Asn).

Identity of any sequence with the sequence of this invention refers to the identity with the entire sequence of the present invention. Sequence identity may be determined by any conventional bioinformatic method, for example by using BLAST (Basic Local Alignment Search Tools) or FASTA (FAST-All).

The present invention also relates to any variants or fragments of the novel beta-lactamases. As used herein, a fragment or variant of the beta-lactamase refers to any part or variant, which has a biological function i.e. is enzymatically active. A variant refers to a peptide having small alterations in the peptide sequence, e.g. mutations, small deletions or insertions. The fragments and variants should include the hydrophilic amino acid at a position corresponding to position 276 according to Ambler classification. The hydrophilic amino acid is typically other than aspartic acid (D).

There are various short forms of the beta-lactamase, which are obtainable from SEQ ID NO: 3 and which are secreted outside the cell. These are called exoforms. The exoforms are the result of hydrolytic activity of proteases in the cell wall or culture medium.

D276X, D276N, D276R, mutant form, P1A derivate or P3A, as used herein encompasses any beta-lactamase active fragment and/or variant of the SEQ ID NO: 3 or variant comprising the explicitly given amino acid sequence (SEQ ID NO: 1). Especially, the beta-lactamase of the invention is an NH$_2$-truncated form, which means that it has been truncated at the aminoterminus. In addition to the NH$_2$-truncation, it may comprise one or more further amino acid deletions, substitutions and/or insertions, as long as it has beta-lactamase activity. Said modifications may be either naturally occurring variations or mutants, or artificial modifications introduced e.g. by gene technology.

Differently aminoterminally truncated exoforms have been found in the growth medium of *B. licheniformis*. Such exoforms are also encompassed herein. Matagne et al. have described various extents of microheterogeneity in extracellular forms produced by the natural host *B. licheniformis* 749/C (Matagne A. et al., 1991. Biochem J. 273:503-510). The following five different secreted exoforms with different N-terminal amino acid residues were identified:

```
(SEQ ID NO: 11)SQPAEKNEKTEMKDD...KALNMNGK(SEQ ID NO: 16)

(SEQ ID NO: 12)EKTEMKDD...KALNMNGK(SEQ ID NO: 16)

(SEQ ID NO: 13)KTEMKDD...KALNMNGK(SEQ ID NO: 16)

(SEQ ID NO: 14)EMKDD...KALNMNGK(SEQ ID NO: 16)

(SEQ ID NO: 15)MKDD...KALNMNGK(SEQ ID NO: 16)
```

Initial amino acid residues are presented in bold. The C-terminal amino acid residues are indicated to the right. The exoform starting from serine (S) is called the "large secreted form" of *B. licheniformis* beta-lactamase, and the one starting from lysine (K) is called the "small secreted form".

The first alpha helix ($\alpha_1$-helix) starts from aspartatic acid (D) (presented in italics) and the end of the last alpha helix ($\alpha_{11}$-helix) ends at asparagine (N) (presented in italics). According to one embodiment of the invention the beta-lactamase comprises at least the amino acids 1-258 of SEQ ID NO: 1 or amino acids 7-264 of SEQ ID NO: 3, which take part in the secondary structure of the protein (Knox J. R. et al., 1991. J. Mol Biol. 220: 435-455). According to another embodiment of the invention one or more of said amino acids 1-258 of SEQ ID NO: 1 or amino acids 7-264 of SEQ ID NO: 3 have been deleted or replaced.

According to still another embodiment of the invention the amino terminal of the beta-lactamase begins with NH$_2$—KTEMKDD (amino acids 4-10 of SEQ ID NO: 3). This so-called ES-betaL exoform may further lack up to 21 contiguous residues as described by Gebhard et al. (Gebhard L. G. et al., 2006, J. Mol. Biol. 21:358(1)280-288). According to another embodiment of the invention the amino terminal begins with glutamic acid (E) of SEQ ID NO: 3, and especially it begins with NH$_2$-EMKDD (amino acids 6-10 of SEQ ID NO: 3), or alternatively it begins with NH$_2$-MKDD (amino acids 7-10 of SEQ ID NO: 3 or amino acids 1-4 of SEQ ID NO: 1).

The variable region in the amino terminal sequence of the beta-lactamase has no rigid structure which accounts for the constancy of enzymatic parameters of various beta lactamase forms.

The four last amino acids at the carboxylic end of the beta-lactamase, MNGK—COOH (amino acids 265-268 of SEQ ID NO: 3), are not part of the secondary structure, and may therefore also be deleted without loosing activity. In another embodiment up to nine C-terminal amino acids may be deleted. C-truncated forms of the protein have been described by Santos et al. (Santos J. et al., 2004. Biochemistry 43:1715-1723).

All the different forms of the beta-lactamase set forth above are encompassed by the present invention, together with other forms of the protein having beta-lactamase activity.

A polynucleotide of the invention may comprise or have a sequence of any one of SEQ ID NO: 2 or 4 or a degenerate thereof. A polynucleotide that is a degenerate of a sequence shown in any one of SEQ ID NO:s 2 or 4 refers to a polynucleotide that has one or more different nucleotides compared to SEQ ID NO:s 2 or 4 but encodes for the same amino acid. Preferably, the nucleotide triplet nnn of SEQ ID NO: 2 or 4 encodes a hydrophilic amino acid, most preferably N or R. A "polynucleotide" as used herein is a sequence of nucleotides such as a DNA or RNA sequence, and may be a single or double stranded polynucleic acid. The term polynucleotide encompasses genomic DNA, cDNA and mRNA.

According to a specific embodiment of the invention, the polynucleotide has at least 30, 35, 40, 41, 42, 43, 44, 45, 46, 47, 48, 49, 50, 51, 52, 53, 54, 55, 56, 57, 58, 59, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8 or 99.9% identity to any one of the nucleotide sequences of SEQ ID NO: 2 or 4, or fragments thereof.

In one specific embodiment of the invention the polynucleotide has a sequence shown in any one of the sequences SEQ ID NO: 2 or 4.

Amino Acids at Position 276 (Ambler) of Class a Beta-Lactamases

Asparagine (Asn, N) at amino acid position 276 is present in a wide variety of class A beta-lactamases. The function of Asn276 has been intensively studied in TEM and SHV beta-lactamases, in which Asn276 forms hydrogen bonds with the guanidium group of arginine (Arg. R) 244 and thus, limits the mobility of the Arg244 side chain.

Substitutions of asparagine (Asn, N) in TEM or SHV enzymes have been recognised as one major contributor to resistance to serine beta-lactamase inhibitors such as clavulanic acid sulbactam or tazobactam. N276D (Asp) substitution variants of TEM-1 beta-lactamase are present in inhibitor resistant beta-lactamases (IRT enzymes such as TEM-35 and TEM-36). An N276D variant is more resistant to clavulanic acid and tazobactam than the wild type TEM-1 enzyme, but concomitantly the catalytic efficiencies (kcat/Km) of N276D variant for various penicillins are less than 50% of those in the TEM-1 wild type enzyme. Catalytic efficacies of the N276D variant to cephalosporins are reduced compared to those of the wild type TEM-1 (Saves I et al., 1995, J Biol Chem. 270:18240-18245).

Similarly to TEM-1, N276D substitution in SHV-1 or SHV-5 beta-lactamase enhances the resistance to serine beta-lactamase inhibitors but reduces their hydrolytic efficiencies to most beta-lactams (Giakkoupi P. et al., 1999, J Antimicrobiol Chemother, 43: 23-29). Furthermore, N276D substitution in SHV-1 or SHV-5 enzymes moderately improves their ability to degrade "fourth generation" cephalosporins cefpirome and cefepime.

In SHV type beta-lactamase OHIO-1, an N276G (Gly) mutant has shown to be highly resistant to clavulanic acid, whereas a TEM-1 derived N276G mutant possesses only moderate resistance to clavulanic acid (Bonomo R A et al., 1995. Biochim Biophys Acta. 1247:121-125).

In the family of CTX-M enzymes, arginine (Arg, R) is typically present at position 276 (Bonnet R., 2004, Antimicrob Agents Chemother, 48: 1-14) and mutations of Arg276 affect the extension of enzyme activity. Relative hydrolysis rates of CTX-M enzymes against cefotaxime are moderately reduced by substitution of Arg276. Furthermore, Arg276Trp, Arg276Cys, Arg276Ser and Arg276Gly CTX-M mutant enzymes do not affect the level of beta-lactamase inhibitor resistance (Bonnet R., 2004, Antimicrob Agents Chemother. 48: 1-14; Perez-Llarena F. J. et al., 2008. J Antimicrobiol Chemother, 61: 792-797).

TABLE 1

Amino acid residues located at 276 position (Ambler classification) among class A beta-lactamases (Matagne A et al., 1998, Biochem J 330: 581-598; Tranier S. et al., 2000, J Biol Chem, 275: 28075-28082)

| Typical beta-lactamase | Typical amino acid residue at position 276 |
|---|---|
| Len-1, SHV-1, TEM-1, PSE-3/PSE-3, ROB-1 | Asn (N) |
| *Bacillus cereus* 5/B type 1 | |
| *Bacillus cereus* 569/H type 1 | |
| *Bacillus anthrasis* sp | |
| *Bacillus licheniformis* PenP beta-lactamase | Asp (D) |
| *Bacillus cereus* 569/H type 3 beta-lactamase | |
| *Bacillus weihenstephanensis* beta-lactamase | |
| *Bacillus clausii* beta.lactamase | |
| *Staphylococcus aureus* PC1 beta-lactamase | |
| Sme-1 NmcA IMI-1 beta-lactamases | |
| CTX-M enzymes | Arg (R) |
| PER-1, VEB-1, CME-1 beta-lactamases | Glu (E) |

Now, in the present invention, the beta-lactamases comprising an amino acid sequence having at least 60% sequence identity with SEQ ID NO: 1 (*Bacillus licheniformis* PenP derivate, i.e. P1A derivate) and having a hydrophilic amino acid residue at a position of SEQ ID NO: 1 corresponding to position 276 according to Ambler classification, show an extended beta-lactam spectrum as well as improved catalytic effects on beta-lactams.

Before, the role of amino acid substitutions of aspartic acid (D) at position 276 in resistance to serine beta-lactamase inhibitors or in catalytic properties to various beta-lactams have not been studied among *Bacillus* spp. beta-lactamases, specifically *B. licheniformis* beta-lactamase.

As used herein, the amino acid residue 276 according to Ambler classification corresponds to amino acid position 243 of SEQ ID NO: 1 and amino acid position 249 of SEQ ID NO: 3.

Typically the beta-lactamases of the present invention have a hydrophilic amino acid at a position corresponding to position 276 of Ambler classification other than aspartic acid (D). Amino acids are classified based on the chemical and/or structural properties of their side chains. The amino acid classification groups include hydrophilic amino acids, which are divided into following groups: polar and positively charged hydrophilic amino acids: polar and neutral of charge hydrophilic amino acids; polar and negatively charged hydrophilic amino acids; aromatic, polar and positively charged hydrophilic amino acids. As used herein "hydrophilic amino acid" includes all above-mentioned groups of hydrophilic amino acids, i.e. refers to polar and positively charged hydrophilic amino acids, to polar and neutral of charge hydrophilic amino acids, to polar and negatively charged hydrophilic amino acids and/or to aromatic, polar and positively charged hydrophilic amino acids (http://www.biomed.curtin.edu.au/biochem/tutorials/AAs/AA.html). "A polar and positively charged hydrophilic amino acid" refers to arginine (R) or lysine (K). "A polar and neutral of charge hydrophilic amino acid" refers to asparagine (N), glutamine (Q), serine (S) or threonine (T). "A polar and negatively charged hydrophilic amino acid" refers to aspartate (D) or glutamate (E). "An aromatic, polar and positively charged hydrophilic amino acid" refers to histidine (H).

In one embodiment of the invention, the hydrophilic amino acid is a neutral or positively charged hydrophilic amino acid selected from the group consisting of arginine (R), histidine (H), lysine (K), asparagine (N), glutamine (Q), serine (S) and threonine (T) at a position of Seq ID No 1 corresponding to position 276 according to Ambler classification.

In a preferred embodiment of the invention, the hydrophilic amino acid of the beta-lactamase at a position of SEQ ID NO: 1 corresponding to position 276 according to Ambler classification is selected from polar and positively charged hydrophilic amino acids from the group consisting of arginine (R), histidine (H) and lysine (K). Most preferably, the amino acid at the position of SEQ ID NO: 1 corresponding to position 276 according to Ambler classification is arginine.

In another preferred embodiment of the invention, the hydrophilic amino acid is selected from polar and neutral of charge hydrophilic amino acids from the group consisting of asparagine (N), glutamine (Q), serine (S) and threonine (T). Most preferably, the amino acid at the position of SEQ ID NO: 1 corresponding to position 276 is asparagine.

Figure 1:
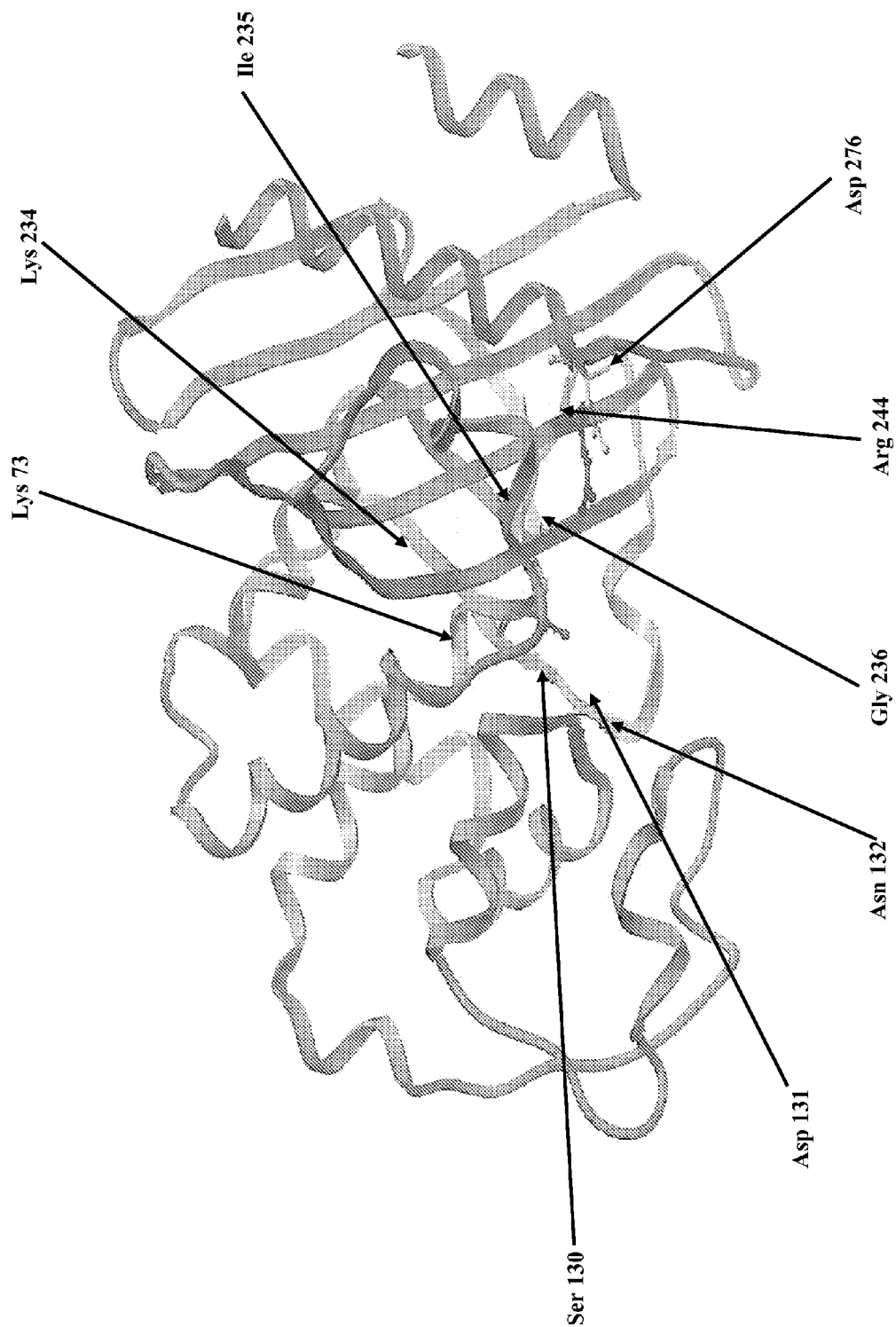
FIG. 1 shows the 30 structure of beta-lactamase of *Bacillus licheniformis* beta-lactamase (small exo form of PenP). The conserved amino acid residues and the side chains residues of R-244 and D-278 are marked. The diagram was generated by using MolSof-Browser programme.

In a further preferred embodiment of the invention, the hydrophilic amino acid at the position of SEQ ID NO: 1 corresponding to position 276 locates in an alpha helix. An alpha helix is a motif of protein secondary structure, resembling a coiled conformation. Alpha helixes may have particular significance in DNA binding motifs (e.g. helix-turn-helix, leucine zipper and zinc finger motifs). In a preferred embodiment of the invention, amino acid residue 276 is located at the final alpha helix$_1$ (FIG. 1). This alpha helix$_{11}$ is not conserved among Class A beta-lactamases.

Specific Features of Class a Beta-Lactamases

One specific feature of class A beta-lactamases is a guanidinium group of Arg278. CTX-M enzymes have Arg278, Arg244 or Arg220, which lies in equivalent positions in the three dimensional structures. Arginine at position 220 or 244 is shown to be essential for the catalytic properties of TEM-1 (Leu220 and Arg244) and *Streptococus albus* G beta-lactamase (Arg220 and Asn244). A basic guanidinium group of arginine 244 or arginine 220 is proposed to contribute the binding of beta-lactam or the inactivation chemistry of "suicide" inhibitors such as clavulanic acid (Matagne et al., 1998, Biochem J. 330:582-598; Perez-Llarena et al., 2008, J Antimicrobiol Chemother, 61: 792-797). In *B. licheniformis* PenP, Arg-244 residue forms a salt bond with aspartic acid 276 (Herzberg, O. 1991, J Mol Biol. 217: 701-719; Knox, J. R., and P. C. Moews, 1991, J Mol Biol. 220: 435-555).

In a preferred embodiment of the invention, the beta-lactamase further comprises at least one amino acid selected from the group consisting of Leu220 and Arg244 according to Ambler classification, which correspond to Leu189 and Arg212, respectively of SEQ ID NO:1.

*Bacillus licheniformis* Beta-Lactamase (PenP, P1A)

The beta-lactamase of the invention originates from *Bacillus licheniformis* 749/C strain. *B. licheniformis* 749/C beta-lactamase (PenP; penicillin amido-beta-lactamhydrolase, EC3.5.2.6) belongs to a subgroup 2a in functional classification of class A beta-lactamases (Bush K. et al., 1995, Antimicrob Agents Chemother 39: 1211-1233). *B. licheniformis* beta-lactamase can be considered as a penicillinase, which has high hydrolytic capacity to degrade e.g. penicillin, ampicillin, amoxicillin or piperacillin and it is generally inhibited by active site-directed beta-lactamase inhibitors such as clavulanic acid, sulbactam or tazobactam (Bush K. et al., 1995, Antimicrob Agents Chemother. 39: 1211-1233).

*Bacillus licheniformis* 749/C beta-lactamase is expressed as a pre-protein of 307 amino acid residues. After translocation and removal of its 26 amino acid residues long signal sequence, it becomes a membrane-anchored lipoprotein in which the aminoterminal cysteine (C27) forms a thioether bond with a diacylglyseride. *B. licheniformis* beta-lactamase is also found as secreted (extracellular) forms which are proteolytic products of the lipoprotein form (Izui K. et al., 1980, Biochemistry 19: 1882-1886; Matagne A. et al, 1991, Biochem J, 273: 503-510). The region of the *Bacillus licheniformis* 749/C beta-lactamase gene encoding the small, secreted form (small exo form; P1A) of amino acid residues 43-307 has been chosen as a DNA fragment for tailoring of host-vector *Bacillus subtilis* production system (WO 2008065247).

Function

Beta-lactamases hydrolyse beta-lactam antibiotics comprising a beta-lactam ring such as penicillins, cephalosporins, clavams (or oxapenams), cephamycins and carbapenems. In a preferred embodiment of the invention, the beta-lactamase hydrolyses penicillins and/or cephalosporins. "Penicillins" refer to several natural or semisynthetic variants of penicillin, which is originally derived from *Penicillium*. Penicillins include but are not limited to amoxicillin, ampicillin, azlocillin, carbenicillin, cloxacillin, dicloxacillin, flucloxacillin, hetacillin, oxacillin, mezlocillin, penicillin G, penicillin V, and piperacillin.

In cephalosporins, the beta-lactam ring is fused to a six-membered dihydrothiazine ring rather than to the five-membered thiazolidine ring found in penicillins. Based on their biological activity, cephalosporins are divided into six generations but some cephaloporins have not been grouped to a particular generation. In one specific embodiment of the invention, the beta-lactamase has improved catalytic efficiency on cephalosporins compared to wild type beta-latamases. According to present invention, Bacillus licheniformis beta-lactamase, in which the aspartic acid (Asp, D) at position 276, numbered in accordance with Ambler classification, is substituted with a hydrophilic amino acid residue such as an asparagine (N) or arginine (R), exhibits an extended activity to beta-lactam antibiotics such as cephalosporins.

In one embodiment of the invention, the cephalosporins are selected from the group consisting of cefoperazone, ceftriaxone and cefazoline.

As used herein, catalytic efficiency of beta-lactamases refers to the ability to hydrolyse beta-lactam antibiotics. Improved catalytic efficiency can be measured by any conventional in vitro, ex vivo or in vivo-methods from any biological sample or a subject.

Methods of Producing and Modifying Beta-Lactamases

The beta-lactamase of the invention may be produced by modifying the enzyme with any conventional method of genetic engineering. Methods such as rational design, random mutagenesis, DNA shuffling (random recombination), phage display, whole-genome shuffling, heteroduplex, random chimeragenesis on transient templates assembly of designed oligonucleotides, mutagenic and unidirectional reassembly, exon shuffling, Y-ligation-based block shuffling, nonhomologous recombination, combination rational design with directed evolution may be utilized in the production. Furthermore, the mutant enzymes may be obtained by employing site-directed mutagenesis and splicing by overlap extension techniques.

In one embodiment of the invention, a method of modifying a beta-lactamase comprises a step of modifying the beta-lactamase comprising an amino acid sequence having at least 60% sequence identity with SEQ ID NO: 1 by replacing an amino acid at a position of SEQ ID NO: 1 corresponding to position 276 according to Ambler classification with a hydrophilic amino acid. The hydrophilic amino acid may be any hydrophilic amino acid, for example selected from the group consisting of arginine (R), histidine (H), lysine (K), asparagine (N), glutamine (Q), serine (S) and threonine (T).

In one embodiment of the invention a non-hydrophilic amino acid is replaced with a hydrophilic amino acid at a position of SEQ ID NO: 1 corresponding to position 276 according to Ambler classification.

The beta-lactamase of the invention can also be produced for example by synthetic methods e.g. peptide synthesis or by recombinant production in a host cell. In a preferred embodiment of the invention, the enzyme is recombinant. As used herein, "recombinant" genetic material refers to a material, which is typically a combination of genetic material, e.g. DNA strands of various origin, and it has been produced by combining or inserting the sequences. The polynucleotide of the invention may for example be inserted under the control of any endogenous or exogenous regulators, such as promoters. Recombinant protein is derived from recombinant DNA.

At least one polynucleotide or polynucleotide fragment of interest may be isolated from a cell or produced synthetically. This polynucleotide or polynucleotide fragment can be transformed to a host cell. A suitable host cell for producing any peptide of the invention may be any eukaryotic or prokaryotic cell, preferably bacteria, most preferably Bacillus spp. strain such as Bacillus subtilis, Bacillus licheniformis, Bacillus pumilis, or Bacillus amyloliquefaciens.

As used herein, "transformation" refers to a genetic alteration of a cell by foreign genetic material, preferably DNA, resulting in expression of this genetic material. The foreign genetic material can be introduced as such or as incorporated into any other genetic material such as vectors, plasmids etc. Any method of genetic engineering or any molecular cloning methods can be used for transforming a host cell with the polynucleotide of the invention. There are various methods of introducing foreign material into a eukaryotic cell. Materials such as polymers (e.g. DEAE-dextran or polyethylenimine), liposomes and nanoparticles (e.g. gold) have been used as carriers for transformation. Genetic material can also be introduced into cells by using for example viruses or vectors as carriers. Other methods for introducing foreign material into a cell include but are not limited to nucleofection, electroporation, conjucation, transfection, sonoporation, heat shock and magnetofection.

After a host cell has produced the peptide of the invention in appropriate conditions, the peptide can for example be purified from the cell or a secreted form of the peptide can be recovered e.g. from culture media. In a preferred embodiment of the invention, the beta-lactamase is secreted.

Pharmaceutical Composition

The pharmaceutical composition of the invention comprises the beta-lactamase of the invention. The composition may comprise only one beta-lactamase or more, such as at least two, three, four etc. different beta-lactamases.

The pharmaceutical compositions of the invention may also comprise any other active ingredients than beta-lactamases of the invention.

The pharmaceutical compositions may be used for example in solid, semisolid or liquid form such as in the form of tablets, pellets, capsules, solutions, emulsions or suspensions. Preferably the composition is for oral administration or for enteral applications.

In addition to at least one beta-lactamase of the invention or polynucleotides or host cells comprising the polynucleotides of the invention, the pharmaceutical composition may comprise pharmaceutically acceptable carrier(s), adjuvant(s), excipient(s), auxiliary excipient(s), antiseptic(s), stabilizing agent(s), binding agent(s), filling agent(s), lubricating agent(s), suspending agent(s), plasticizer, colorants, film formers, sugar, alcohols, glidant agents and diluent agents and/or components normally found in corresponding products.

The product or pharmaceutical composition of the invention comprises the beta-lactamases in an amount sufficient to produce the desired effect.

The products or pharmaceutical compositions may be manufactured by any conventional processes known in the art. The beta-lactamases may be added to any pharmaceutical product or mixed with any agents during any preparation step. The beta-lactamase of the invention may also be produced for example by expressing the beta-lactamase gene in appropriate conditions in a pharmaceutical product or in the target tissue after the pharmaceutical product has degraded.

In one preferred embodiment of the invention, the beta-lactamase(s) and the beta-lactam antibiotic are administered together in the form of an enteric coated pellet to a subject. Aqueous-based coating forms appear to be the most favourable materials for coating processes of the hydrophilic P1A protein. The aqueous polymers commonly used to achieve enteric properties, and also usable in the present invention, are polymethacrylates such as Eudragit®, cellulose based polymers e.g. cellulose ethers e.g. Duodcell®, or cellulose esters, e.g. Aquateric®, or polyvinyl acetate copolymers e.g. Opadry®.

Beta-lactamase of the invention or a pharmaceutical composition of the invention may be administered to a subject simultaneously or sequentially with a beta-lactam antibiotic. In one embodiment of the invention, the beta-lactamase or the pharmaceutical composition is administered before a beta-lactam antibiotic, for example 5 to 30 minutes before a beta-lactam antibiotic. The beta-lactamase and a beta-lactam antibiotic/antibiotics may be in the same formulation or in different formulations.

Adverse Effects of Beta-Lactams and Treatments

Adverse effects i.e. adverse drug reactions for the beta-lactam antibiotics may include but are not limited to diarrhea, nausea, rash, urticaria, superinfection, fever, vomiting, erythema, dermatitis, angioedema and pseudomembranous colitis.

In a preferred embodiment of the invention, the adverse effects to be treated or prevented occur in the gastrointestinal tract (GIT). As used herein, gastrointestinal tract refers to digestive structures stretching from the mouth to the anus. The gastrointestinal tract comprises the mouth, esophagus, stomach, duodenum, jejunum, ileum, small intestine, colon, cecum, rectum and anus.

The beta-lactamase of the invention or the pharmaceutical composition of the invention may be administered to a subject orally or directly to the gastrointestinal tract. Drug product(s) of enzyme combinations are intended to inactivate unabsorbed beta-lactam in the GIT or in other undesired body compartments such as skin or vaginal cavity. The pharmaceutical composition may be an orally administered drug product, a dermatological formulation or a vaginal suppository, and may comprise liquid, immediate, delayed or sustained release dosage formulations.

In one preferred embodiment of the invention, the beta-lactamase(s) is/are administered orally. In another preferred embodiment of the invention, the beta-lactamase(s) is/are administered directly to the gastro-intestine of a patient.

A treated subject may be a man or an animal such as a pet or production animal e.g. dog, cat, cow, pig, chicken or horse. In a preferred embodiment of the invention, the subject is a man.

The present invention is illustrated by the following examples, which are not intended to be limiting in any way.

Example 1. Construction of D276N and D276R Mutant Enzymes

*Bacillus licheniformis* beta-lactamase D276N and D276R mutants were constructed by splicing-by-overlap extension mutagenesis (SOE) using the pRSH10 plasmid encoding P1A beta-lactamase as a template for the initial PCR reactions according to previously published procedures (Horton R. M. et al., 1989, Gene 77:61-68). Primers were designed to provide two different PCR products with a region of common sequence. Fragments were then fused in a subsequent PCR amplification by aid of overlapping regions. The desired mutations were achieved by using mutagenic primers in initial PCR.

For the D276N mutant, mutation was made at the desired position in wild type gene, converting a GAT codon to a AAT codon. The primers utilized in the first PCR amplifications are presented in Table 2. The size of amplified fragments in the first PCR was 800 nt and 220 nt which have a 21 nt long overlapping region.

TABLE 2

Oligonucleotide PCR primers. Complementary regions are shaded and mutated codons are expressed as bold. Forward-1 and reverse-1 primers were used in amplification of fused fragment in the second PCR.

| Size of PCR fragment (nt) | Oligonucleotide primers |
|---|---|
| 800 | Forward-1: 5'-CGA TTG TTT GAG AAA AGA-3' (SEQ ID NO: 5)<br>Reverse-D276N: 5'-AAT AAG TTT ATT ATC ATA CTT GGC GTC CT-3' (SEQ ID NO: 6)<br>Reverse-D276R: 5'-AAT AAG TTT GCG ATC ATA CTT GGC GTC CT-3' (SEQ ID NO: 7) |
| 220 | Forward-D276N: 5'-AAG TAT GAT AAT AAA CTT ATT GCA GAG G-3' (SEQ ID NO: 8)<br>Forward-D276R: 5'-AAG TAT GAT CGC AAA CTT ATT GCA GAG G-3' (SEQ ID NO: 9)<br>Reverse-1: 5-GTA TTT GTC ACA CCT GAT G-3' (SEQ ID NO: 10) |

In the second PCR reaction (SOE reaction), the two overlapping fragments were fused together in a subsequent extension reaction. The inclusion of outside primers (Forward-1 and Reverse-1) in the extension reaction amplifies the fused product by PCR. The purified SOE product was digested with HindIII restriction enzyme and ligated to HindIII cleaved pKTH141 secretion vector as described in WO 2008/065247.

Competent cells of *Bacillus subtilis* RS303 were transformed with a ligation mixture. Positive clones on Luria-kanamycin plates were screened by suspending bacterial mass of a single colony into nitrocefin solution. Positive clones effectively hydrolyzed nitrocefin turning the colour of nitrocefin solution from yellow to red. Hybrid plasmid was purified from cells of a single clone. The correct sequence of PCR generated region was verified by DNA sequencing.

For the D276R mutant, mutation was made at the desired position by converting a GAT codon to a CGC codon. Construction of D276R mutant strain was performed similar to that of D276N mutant except reverse-D276R- and forward-D276R-primers were used in the initial PCR (see Table 2).

Example 2. Nucleotide Sequence of D276N Mutant Beta-Lactamase Gene (penP)

The expression construct was isolated from a positive clone and the insert was subjected to DNA sequencing. The complete nucleotide sequence and deduced amino acid sequences of D276N mutant beta-lactamase gene revealed that a substitution of Asp for Asn has occurred correctly at the desired codon (FIG. 2). Furthermore, the DNA sequence of D276N mutant beta-lactamase gene revealed in frame fusion between nucleotide sequence encoding a 31 amino acid long signal sequence of *Bacillus amyloliquefaciens* alpha amylase, the HindIII cloning site and the complete sequence of D276N mutant gene. The signal peptidase is predicted to cut the peptide bond between alanine (A) at position of −1 and glutamine (Q) at position of +1. The mature D276N beta-lactamase possesses an $NH_2$-terminal extension of a $NH_2$-QAS-tripeptide derived from the Hind III cloning site in the expression construct. Hence, based on the deduced amino acid sequence the mature D276N mutant beta-lactamase is comprised of 268 amino acid residues.

Example 3. Nucleotide Sequence of D276R Mutant Beta-Lactamase Gene (penP)

To confirm the desired substitution of aspartic acid to arginine at position 276 (Ambler classification) in the *Bacillus licheniformis* beta-lactamase gene, the expression construct was isolated from a positive clone and the nucleotide sequence of the insert was sequenced similar to example 2.

According to the obtained nucleotide sequence, the deduced amino acid sequence contains the desired D276R substitution and the mature D276R mutant enzyme is comprised of 268 amino acid residues (FIG. 3).

Example 4. Biochemical Analysis of D276N Mutant Beta-Lactamase (P3A)

The purity of the enzyme preparate was estimated to more than 95 percentages by SDS-PAGE analysis (data not shown).

Kinetic parameters of the wild type (P1A) and D276N (P3A) mutant *B. licheniformis* beta-lactamases were determined for hydrolysis of various types of beta-lactams and are summarized in Table 3. Enzymatic reactions were performed in 20 mM phosphate buffer (pH 7) at 30° C. by using appropriate enzyme concentration and various concentrations of penicillin or cephalosporin substrates. The $k_{cat}$ and $K_m$ values were obtained with the aid of the Hanes linearization method. The main results are described below.

(i) Penicillins

The effect of the D276N substitution on the hydrolysis of penicillins (ampicillin amoxicillin or piperacillin) was not drastic with enzymatic efficiencies of 51-80 percentages of those of the wild type enzyme. Consequently, $k_{cat}/K_m$ values of D276N mutant enzyme for penicillins were reduced as a maximum of two folds or less.

(ii) Cephalosporins

As expected, related to penicillins, the wild type beta-lactamase had poor enzymatic efficiencies for various cephalosporins including the first (cafazoline), the second (cefuroxime), and the third (ceftriaxone, cefotaxime, ceftadizime, cefoperazone, and cefepime) generation cephalosporins (Table 1). Surprisingly, the enzymatic efficiencies of D276N mutant enzyme for certain cephalosporins, preferably for cefoperazone and more preferably for ceftriaxone, were essentially improved compared to those obtained with wild type enzymes. The $K_m$ constants for ceftriaxone and cefoperazone were decreased and concomitantly the turnover numbers ($k_{cat}$) for ceftriaxone and cefoperazone were increased compared to those of the wild type enzyme (P1A). Thus the aspartic acid-asparagine substitution at position 276 of *Bacillus licheniformis* beta-lactamase contributes the extension of beta-lactam substrate profile in *Bacillus licheniformis* beta-lactamase.

TABLE 3

Kinetic parameters for hydrolysis of beta-lactam substrates by wild type (P1A) and D276N mutant enzymes of *Bacillus licheniformis* beta-lactamases.

| Beta-lactam | Wild type beta-lactamase (P1A) | | | D276N mutant | | | Relative catalytic efficacies (%)[1] |
|---|---|---|---|---|---|---|---|
| | $K_m$ (μM) | $k_{cat}$ ($s^{-1}$) | $k_{cat}/K_m$ ($μM^{-1} s^{-1}$) | $K_m$ (μM) | $k_{cat}$ ($s^{-1}$) | $k_{cat}/K_m$ ($μM^{-1} s^{-1}$) | |
| Ampicillin | 157 | 3369 | 21.45 | 161 | 2160 | 13.42 | 63 |
| Piperacillin | 49 | 939 | 19.16 | 53 | 816 | 15.40 | 80 |
| Amoxicillin | 119 | 2959 | 24.84 | 219 | 2789 | 12.74 | 51 |
| Ceftriaxone | 400 | 0.045 | 0.00013 | 38 | 83 | 2.18 | 1676923 |
| Cefotaxime | 363 | 246 | 0.67 | 213 | 36 | 0.17 | 25 |
| Ceftadizime | 0 | 0 | 0 | 1505 | 2.74 | 0.0018 | |
| Cefepime | 0 | 0 | 0 | 1357 | 133 | 0.1 | |
| Cafazoline | 22 | 93 | 4.22 | 37 | 192 | 5.19 | 123 |
| Cefoperazone | 7 | 10 | 1.43 | 2 | 17 | 8.2 | 573 |
| Cefuroxime | 107 | 233 | 2.18 | 277 | 35 | 0.13 | 6 |

[1]Relative catalytic efficiency ($k_{cat}/K_m$) of D275N compared to that of the wild type enzyme (P1A).

Example 5. Biochemical Characterization of D276R Mutant Enzyme

D276R mutant enzyme was constructed to evaluate whether Asp-276 tolerates substitutions and assesses the contribution of D276R substitution to the extension of beta-lactamase activity observed in D276N enzyme.

Crude enzyme samples of D276R and D276N obtained from culture supernatants were employed as test materials. The purity and quantity of enzyme samples were estimated by performing SDS-PAGE-analysis. Hydrolysis rate of D276R and D276N mutant enzymes for various beta-lactams were performed by determining $V_{max}$ values. Obtained results are presented as relative activities (%) compared to those of D276N enzyme in Table 4.

In general, catalytic efficiencies of D276R beta-lactamase for both penicillins and cephalosporins are comparable to those of D276N enzyme. In comparison with D276N enzyme, D276R enzyme has reduced activity to ceftriaxone and improved activity to cefoperazone. This study showed that the extended spectrum of beta-lactams can be achieved by substituting a hydrophilic amino acid residue such as arginine or asparagine for aspartic acid at position 276 in the *Bacillus licheniformis* beta-lactamase. It also indicates that a desired enzyme modification can be achieved by substituting another hydrophilic amino acid residue such as glutamine (Q), lysine (K), serine (S) or threonine (T) for aspartic acid at position 276.

TABLE 4

Relative activities (%) of D276R mutant enzyme compared to those of D276N mutant enzyme

| Beta-lactam | Relative activities |
| --- | --- |
| Ampicillin | 82 |
| Piperacillin | 84 |
| Amoxicillin | 71 |
| Ceftriaxone | 50 |
| Cefotaxime | 105 |
| Ceftadizime | — |
| Cefepime | 74 |
| Cefazoline | 84 |
| Cefoperazone | 232 |
| Cefuroxime | 99 |

Example 6. In Vivo Study of D276N Beta-Lactamase

The capability of *Bacillus licheniformis* D276N mutant beta-lactamase enzyme to inactivate ceftriaxone (CRO) which has been excreted into the gastrointestinal tract during parenteral therapy was investigated in a dog model. Laboratory beagles of the study have a nipple valve surgically inserted in jejunum approximately 170 cm distal to pylorus enabling collection of samples for the analysis. The intestinal surgery did not alter the intestinal motility. Five beagle dogs were utilized in each experiment.

The study was performed as two sequential treatments: In the first treatment (control experiment without beta-lactamase therapy), a single dose of ceftriaxone (30 mg of ceftriaxone (CRO) per kg of body weight which corresponds to about 1 gram dose of CRO in humans) was administered intravenously 20 minutes after the first feeding of the dogs. Jejunal samples were collected at various time points during ten hours. The dogs were fed again five hours and forty minutes after the ceftriaxone administration in order to induce the biliary excretion of ceftriaxone accumulated in gallbladder.

Jejunal chyme samples were immediately frozen and stored at −20° C. to await the analysis. Chyme samples were pretreated with perchloric-citric acid in order to precipitate interfering substances. The precipitates were removed by centrifugation. A reverse-phase high-pressure chromatography method with UV detection was used for the quantification of ceftriaxone in supernatants.

In the second treatment, D276N mutant beta-lactamase was given as enteric coated pellets filled in hard gelatine capsules 10 minutes prior to ceftriaxone injection. Enteric coating dosage forms are common among oral products in pharmaceutical industry. Enteric coating drug products are designed to bypass stomach as an intact form and to release the contents of the dosage form in small intestine. The reasons for applying enteric solid formulations are to protect the drug substance from the destructive action of the enzymes or low pH environment of stomach or to prevent drug substance-induced irritation of gastric mucosa, nausea or bleeding or to deliver drug substance in undiluted form at a target site in small intestine. Based on these criteria, enteric coated drug products can be regarded as a type of delayed action dosage forms. Polymethacrylic acid copolymer Eudragit® L 30 D-55 was employed in order to achieve a pH dependent enteric-coated dosage form. A single dose of enteric coated pellets containing about 0.44 mg of active D276N beta-lactamase per kg of body weight was used in the second treatment.

Obtained results from both treatments are presented in FIG. 4. Treatment 1 showed that high concentrations of ceftriaxone were excreted into the small intestinal tract during the parenteral ceftriaxone therapy. The highest jejunal concentration (about 1500 micrograms per gram of jejunal chyme) was found 60 minutes after the ceftriaxone injection. The increased jejunal ceftriaxone levels were observed after the second feeding of the dogs (at time point 340 minutes) which indicates food stimulated, ceftriaxone containing bile excretion accumulation in gallbladder.

Treatment 2 showed that orally administered D276N mutant beta-lactamase is capable to reduce jejunal ceftriaxone levels near to the limit of quantification (10 micrograms of ceftriaxone per microgram of jejunal chyme). This finding shows that D276N mutant beta-lactamase is a potent drug substance candidate for reducing the side effects related to a use of parenteral ceftriaxone. Moreover, based on high activities to penicillins such as ampicillin, amoxicillin and piperacillin, D276N or D276R mutant enzymes can be used as an alternative drug substance in beta-lactamase therapy described in WO 2008065247.

The invention claimed is:

1. A method for reducing the likelihood of antibiotic-associated diarrhea in a subject, comprising administering an effective amount of a beta-lactamase to the subject wherein:
   the subject is receiving a beta-lactam antibiotic, the beta-lactam antibiotic being a substrate of the beta-lactamase;
   the antibiotic-associated diarrhea is caused by unabsorbed beta-lactam antibiotic in the intestinal tract; and
   the beta-lactamase comprises an amino acid sequence having at least 90% sequence identity with SEQ ID NO: 1 and an asparagine (N) or arginine (R) residue at a position corresponding to position 276 according to Ambler classification and the beta-lactamase hydrolyzes ceftriaxone substantially more efficiently than a beta-lactamase of SEQ ID NO: 1 that has an aspartic acid (D) at a position corresponding to position 276 according to Ambler classification.

2. The method of claim 1, wherein the beta-lactamase hydrolyses a penicillin and a cephalosporin.

3. The method of claim 2, wherein the cephalosporin is selected from cefoperazone and ceftriaxone.

4. The method of claim 1, wherein the beta-lactamase is administered simultaneously to or sequentially with the beta-lactam antibiotic.

5. The method of claim 4, wherein the beta-lactamase is administered before the beta-lactam antibiotic.

6. The method of claim 1, wherein the beta-lactamase is administered orally.

7. The method of claim 1, wherein the beta-lactam antibiotic is administered by intravenous injection.

8. The method of claim 1, wherein the beta-lactam antibiotic is selected from penicillin and cephalosporin.

9. The method of claim 8, wherein the cephalosporin is selected from cefoperazone and ceftriaxone.

10. The method of claim 1, wherein the amino acid sequence has at least 93% sequence identity with SEQ ID NO: 1.

11. The method of claim 1, wherein the amino acid sequence has at least 95% sequence identity with SEQ ID NO: 1.

12. The method of claim 1, wherein the beta-lactamase comprises an amino acid sequence of SEQ ID NO: 1 with an asparagine (N) residue at position 276 according to Ambler classification.

13. The method of claim 1, wherein the beta-lactamase comprises an amino acid sequence of SEQ ID NO: 1 with an arginine (R) residue at position 276 according to Ambler classification.

14. The method of claim 1, wherein the method maintains an ecological balance of normal intestinal microbiota.

* * * * *

SEQUENCE LISTING

<160> NUMBER OF SEQ ID NOS: 18

<210> SEQ ID NO 1
<211> LENGTH: 258
<212> TYPE: PRT
<213> ORGANISM: Bacillus licheniformis
<220> FEATURE:
<221> NAME/KEY: misc_feature
<222> LOCATION: (243)..(243)
<223> OTHER INFORMATION: Xaa can be any naturally occurring amino acid

<400> SEQUENCE: 1

Met Lys Asp Asp Phe Ala Lys Leu Glu Glu Gln Phe Asp Ala Lys Leu

```
            1               5                  10                 15
         Gly Ile Phe Ala Leu Asp Thr Gly Thr Asn Arg Thr Val Ala Tyr Arg
                        20                  25                  30

Pro Asp Glu Arg Phe Ala Phe Ala Ser Thr Ile Lys Ala Leu Thr Val
                        35                  40                  45

Gly Val Leu Leu Gln Gln Lys Ser Ile Glu Asp Leu Asn Gln Arg Ile
                 50                  55                  60

Thr Tyr Thr Arg Asp Asp Leu Val Asn Tyr Asn Pro Ile Thr Glu Lys
          65                  70                  75                  80

His Val Asp Thr Gly Met Thr Leu Lys Glu Leu Ala Asp Ala Ser Leu
                            85                  90                  95

Arg Tyr Ser Asp Asn Ala Ala Gln Asn Leu Ile Leu Lys Gln Ile Gly
                         100                 105                 110

Gly Pro Glu Ser Leu Lys Lys Glu Leu Arg Lys Ile Gly Asp Glu Val
                         115                 120                 125

Thr Asn Pro Glu Arg Phe Glu Pro Glu Leu Asn Glu Val Asn Pro Gly
                 130                 135                 140

Glu Thr Gln Asp Thr Ser Thr Ala Arg Ala Leu Val Thr Ser Leu Arg
         145                 150                 155                 160

Ala Phe Ala Leu Glu Asp Lys Leu Pro Ser Glu Lys Arg Glu Leu Leu
                         165                 170                 175

Ile Asp Trp Met Lys Arg Asn Thr Thr Gly Asp Ala Leu Ile Arg Ala
                         180                 185                 190

Gly Val Pro Asp Gly Trp Glu Val Ala Asp Lys Thr Gly Ala Ala Ser
                         195                 200                 205

Tyr Gly Thr Arg Asn Asp Ile Ala Ile Ile Trp Pro Pro Lys Gly Asp
                 210                 215                 220

Pro Val Val Leu Ala Val Leu Ser Ser Arg Asp Lys Lys Asp Ala Lys
         225                 230                 235                 240

Tyr Asp Xaa Lys Leu Ile Ala Glu Ala Thr Lys Val Val Met Lys Ala
                         245                 250                 255

Leu Asn

<210> SEQ ID NO 2
<211> LENGTH: 774
<212> TYPE: DNA
<213> ORGANISM: Bacillus licheniformis
<220> FEATURE:
<221> NAME/KEY: misc_feature
<222> LOCATION: (727)..(729)
<223> OTHER INFORMATION: n is a, c, g, or t

<400> SEQUENCE: 2
atgaaagatg attttgcaaa acttgaggaa caatttgatg caaaactcgg gatctttgca      60
ttggatacag gtacaaaccg gacggtagcg tatcggccgg atgagcgttt tgcttttgct     120
tcgacgatta aggctttaac tgtaggcgtg cttttgcaac agaaatcaat agaagatctg     180
aaccagagaa taacatatac acgtgatgat cttgtaaact acaacccgat tacggaaaag     240
cacgttgata cgggaatgac gctcaaagag cttgcggatg cttcgcttcg atatagtgac     300
aatgcggcac agaatctcat tcttaaacaa attggcggac tgaaagtttt gaaaaaggaa     360
ctgaggaaga ttggtgatga ggttacaaat cccgaacgat tcgaaccaga gttaaatgaa     420
gtgaatccgg gtgaaactca ggataccagt acagcaagag cacttgtcac aagccttcga     480
gcctttgctc ttgaagataa acttccaagt gaaaaacgcg agcttttaat cgattggatg     540
```

```
aaacgaaata ccactggaga cgccttaatc cgtgccggtg tgccggacgg ttgggaagtg      600
gctgataaaa ctggagcggc atcatatgga acccggaatg acattgccat catttggccg      660
ccaaaaggag atcctgtcgt tcttgcagta ttatccagca gggataaaaa ggacgccaag      720
tatgatnnna aacttattgc agaggcaaca aaggtggtaa tgaaagcctt aaac            774
```

```
<210> SEQ ID NO 3
<211> LENGTH: 299
<212> TYPE: PRT
<213> ORGANISM: Bacillus licheniformis
<220> FEATURE:
<221> NAME/KEY: mat_peptide
<222> LOCATION: (1)..(268)
<223> OTHER INFORMATION: beta-lactamase
<220> FEATURE:
<221> NAME/KEY: MISC_FEATURE
<222> LOCATION: (249)..(249)
<223> OTHER INFORMATION: Xaa can be any naturally occurring amino acid

<400> SEQUENCE: 3
```

```
Met Ile Gln Lys Arg Lys Arg Thr Val Ser Phe Arg Leu Val Leu Met
    -30             -25                 -20

Cys Thr Leu Leu Phe Val Ser Leu Pro Ile Thr Lys Thr Ser Ala Gln
-15                 -10                  -5              -1   1

Ala Ser Lys Thr Glu Met Lys Asp Asp Phe Ala Lys Leu Glu Glu Gln
             5                  10                  15

Phe Asp Ala Lys Leu Gly Ile Phe Ala Leu Asp Thr Gly Thr Asn Arg
         20                  25                  30

Thr Val Ala Tyr Arg Pro Asp Glu Arg Phe Ala Phe Ala Ser Thr Ile
         35                  40                  45

Lys Ala Leu Thr Val Gly Val Leu Leu Gln Gln Lys Ser Ile Glu Asp
50                  55                  60                  65

Leu Asn Gln Arg Ile Thr Tyr Thr Arg Asp Asp Leu Val Asn Tyr Asn
                 70                  75                  80

Pro Ile Thr Glu Lys His Val Asp Thr Gly Met Thr Leu Lys Glu Leu
             85                  90                  95

Ala Asp Ala Ser Leu Arg Tyr Ser Asp Asn Ala Ala Gln Asn Leu Ile
            100                 105                 110

Leu Lys Gln Ile Gly Gly Pro Glu Ser Leu Lys Lys Glu Leu Arg Lys
        115                 120                 125

Ile Gly Asp Glu Val Thr Asn Pro Glu Arg Phe Glu Pro Glu Leu Asn
130                 135                 140                 145

Glu Val Asn Pro Gly Glu Thr Gln Asp Thr Ser Thr Ala Arg Ala Leu
                150                 155                 160

Val Thr Ser Leu Arg Ala Phe Ala Leu Glu Asp Lys Leu Pro Ser Glu
            165                 170                 175

Lys Arg Glu Leu Leu Ile Asp Trp Met Lys Arg Asn Thr Thr Gly Asp
        180                 185                 190

Ala Leu Ile Arg Ala Gly Val Pro Asp Gly Trp Glu Val Ala Asp Lys
    195                 200                 205

Thr Gly Ala Ala Ser Tyr Gly Thr Arg Asn Asp Ile Ala Ile Ile Trp
210                 215                 220                 225

Pro Pro Lys Gly Asp Pro Val Val Leu Ala Val Leu Ser Ser Arg Asp
                230                 235                 240

Lys Lys Asp Ala Lys Tyr Asp Xaa Lys Leu Ile Ala Glu Ala Thr Lys
            245                 250                 255

Val Val Met Lys Ala Leu Asn Met Asn Gly Lys
```

<210> SEQ ID NO 4
<211> LENGTH: 900
<212> TYPE: DNA
<213> ORGANISM: Bacillus licheniformis
<220> FEATURE:
<221> NAME/KEY: misc_feature
<222> LOCATION: (838)..(840)
<223> OTHER INFORMATION: n is a, c, g, or t

<400> SEQUENCE: 4

```
atgattcaaa aacgaaagcg gacagtttcg ttcagacttg tgcttatgtg cacgctgtta      60
tttgtcagtt tgccgattac aaaaacatca gcgcaagctt ccaagacgga gatgaaagat     120
gattttgcaa aacttgagga acaatttgat gcaaaactcg ggatctttgc attggataca     180
ggtacaaacc ggacggtagc gtatcggccg gatgagcgtt ttgcttttgc ttcgacgatt     240
aaggctttaa ctgtaggcgt gcttttgcaa cagaaatcaa tagaagatct gaaccagaga     300
ataacatata cacgtgatga tcttgtaaac tacaacccga ttacggaaaa gcacgttgat     360
acgggaatga cgctcaaaga gcttgcggat gcttcgcttc gatatagtga caatgcggca     420
cagaatctca ttcttaaaca aattggcgga cctgaaagtt tgaaaaagga actgaggaag     480
attggtgatg aggttacaaa tcccgaacga ttcgaaccag agttaaatga agtgaatccg     540
ggtgaaactc aggataccag tacagcaaga gcacttgtca caagccttcg agcctttgct     600
cttgaagata aacttccaag tgaaaaacgc gagcttttaa tcgattggat gaaacgaaat     660
accactggag acgccttaat ccgtgccggt gtgccggacg gttgggaagt ggctgataaa     720
actggagcgg catcatatgg aaccccggaat gacattgcca tcatttggcc gccaaaagga     780
gatcctgtcg ttcttgcagt attatccagc agggataaaa aggacgccaa gtatgatnnn     840
aaacttattg cagaggcaac aaaggtggta atgaaagcct taaacatgaa cggcaaataa     900
```

<210> SEQ ID NO 5
<211> LENGTH: 18
<212> TYPE: DNA
<213> ORGANISM: Artificial Sequence
<220> FEATURE:
<223> OTHER INFORMATION: oligonucleotide PCR primer

<400> SEQUENCE: 5
cgattgtttg agaaaaga                                                    18

<210> SEQ ID NO 6
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 6
aataagttta ttatcatact tggcgtcct                                        29

<210> SEQ ID NO 7
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 7
aataagtttg cgatcatact tggcgtcct                                        29

```
<210> SEQ ID NO 8
<211> LENGTH: 28
<212> TYPE: DNA
<213> ORGANISM: Artificial Sequence
<220> FEATURE:
<223> OTHER INFORMATION: oligonucleotide PCR primer

<400> SEQUENCE: 8
aagtatgata ataaacttat tgcagagg                                      28

<210> SEQ ID NO 9
<211> LENGTH: 28
<212> TYPE: DNA
<213> ORGANISM: Artificial Sequence
<220> FEATURE:
<223> OTHER INFORMATION: oligonucleotide PCR primer

<400> SEQUENCE: 9
aagtatgatc gcaaacttat tgcagagg                                      28

<210> SEQ ID NO 10
<211> LENGTH: 19
<212> TYPE: DNA
<213> ORGANISM: Artificial Sequence
<220> FEATURE:
<223> OTHER INFORMATION: oligonucleotide PCR primer

<400> SEQUENCE: 10
gtatttgtca cacctgatg                                                19

<210> SEQ ID NO 11
<211> LENGTH: 15
<212> TYPE: PRT
<213> ORGANISM: Bacillus licheniformis

<400> SEQUENCE: 11

Ser Gln Pro Ala Glu Lys Asn Glu Lys Thr Glu Met Lys Asp Asp
1               5                   10                  15

<210> SEQ ID NO 12
<211> LENGTH: 8
<212> TYPE: PRT
<213> ORGANISM: Bacillus licheniformis

<400> SEQUENCE: 12

Glu Lys Thr Glu Met Lys Asp Asp
1               5

<210> SEQ ID NO 13
<211> LENGTH: 7
<212> TYPE: PRT
<213> ORGANISM: Bacillus licheniformis

<400> SEQUENCE: 13

Lys Thr Glu Met Lys Asp Asp
1               5

<210> SEQ ID NO 14
<211> LENGTH: 5
<212> TYPE: PRT
<213> ORGANISM: Bacillus licheniformis

<400> SEQUENCE: 14

Glu Met Lys Asp Asp
```

-continued

```
<210> SEQ ID NO 15
<211> LENGTH: 4
<212> TYPE: PRT
<213> ORGANISM: Bacillus licheniformis

<400> SEQUENCE: 15

Met Lys Asp Asp
1

<210> SEQ ID NO 16
<211> LENGTH: 8
<212> TYPE: PRT
<213> ORGANISM: Bacillus licheniformis

<400> SEQUENCE: 16

Lys Ala Leu Asn Met Asn Gly Lys
1               5

<210> SEQ ID NO 17
<211> LENGTH: 4
<212> TYPE: PRT
<213> ORGANISM: Artificial Sequence
<220> FEATURE:
<223> OTHER INFORMATION: beta-lactamase conserved elemet
<220> FEATURE:
<221> NAME/KEY: MISC_FEATURE
<222> LOCATION: (2)..(3)
<223> OTHER INFORMATION: Xaa may be any amino acid

<400> SEQUENCE: 17

Ser Xaa Xaa Lys
1

<210> SEQ ID NO 18
<211> LENGTH: 5
<212> TYPE: PRT
<213> ORGANISM: Bacillus licheniformis

<400> SEQUENCE: 18

Gln Ala Ser Lys Thr
1               5
```